United States Patent [19]
Hess et al.

[11] 4,287,341
[45] Sep. 1, 1981

[54] ALKOXY-SUBSTITUTED-6-CHLORO-QUINAZOLINE-2,4-DIONES

[75] Inventors: Hans-Jurgen E. Hess, Old Lyme; Jasjit S. Bindra; Praful K. Shah, both of Groton, all of Conn.

[73] Assignee: Pfizer Inc., New York, N.Y.

[21] Appl. No.: 126,838

[22] Filed: Mar. 3, 1980

Related U.S. Application Data

[63] Continuation-in-part of Ser. No. 90,313, Nov. 1, 1979, abandoned.

[51] Int. Cl.³ .......................................... C07D 239/96
[52] U.S. Cl. ................................ 544/285; 260/243.3; 260/465 E; 424/251; 544/62; 544/116; 544/284; 544/291; 544/293; 562/453
[58] Field of Search ........................................ 544/285

[56] References Cited

U.S. PATENT DOCUMENTS

| | | | |
|---|---|---|---|
| 3,511,836 | 5/1970 | Hess et al. | 544/291 |
| 3,669,968 | 6/1972 | Hess et al. | 544/291 |
| 3,920,636 | 11/1975 | Takahashi et al. | 424/251 |
| 4,001,237 | 1/1977 | Partyka et al. | 424/251 |
| 4,001,238 | 1/1977 | Partyka et al. | 424/251 |
| 4,026,894 | 5/1977 | Winn et al. | 424/251 |
| 4,060,615 | 11/1977 | Matier et al. | 424/251 |
| 4,101,548 | 7/1978 | Crenshaw et al. | 424/251 |

FOREIGN PATENT DOCUMENTS 1117130 11/1961 Fed. Rep. of Germany ........... 544/285

OTHER PUBLICATIONS

Althuis et al., *J. Med. Chem.*, 20, 146 (1977).

*Primary Examiner*—Paul M. Coughlan, Jr.
*Attorney, Agent, or Firm*—Connolly and Hutz

[57] ABSTRACT 2,4-Diaminoquinazolines of the formula

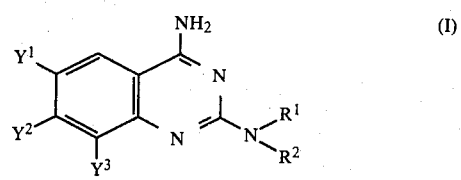

wherein
$Y^1$ is hydrogen or chloro, $Y^2$ is OR, $Y^3$ is hydrogen or OR such that when $Y^1$ is hydrogen, $Y^3$ is OR and when $Y^1$ is chloro, $Y^3$ is hydrogen or OR, and the pharmaceutically acceptable salts thereof; R represents an alkyl group having from one to three carbon atoms;
taken separately, $R^1$ and $R^2$ are each hydrogen, alkyl having from one to five carbon atoms, cycloalkyl having from three to eight carbon atoms, alkenyl or alkynyl each having from three to five carbon atoms or hydroxy substituted alkyl having from two to five carbon atoms, when taken together with the nitrogen atom to which they are attached $R^1$ and $R^2$ form a substituted or unsubstituted heterocyclic group optionally containing an atom of oxygen, sulfur or a second atom of nitrogen as a ring member; their use as antihypertensive agents, pharmaceutical compositions containing them and intermediates for their production.

3 Claims, No Drawings

ALKOXY-SUBSTITUTED-6-CHLORO-QUINAZOLINE-2,4-DIONES

CROSS-REFERENCE TO RELATED APPLICATION

This is a continuation-in-part of application Ser. No. 90,313 filed Nov. 1, 1979, now abandoned.

BACKGROUND OF THE INVENTION

1. Field of the Invention

This invention relates to certain 2,4-diaminoquinazolines. Particularly, the invention relates to certain 7-alkoxy-2,4-diaminoquinazolines which are further substituted by a 6-chloro group and/or an 8-alkoxy group, their use as antihypertensive agents, pharmaceutical compositions thereof and intermediates for their production.

2. Description of the Prior Art

U.S. Pat. Nos. 3,511,836; 3,635,979 and 3,663,706 disclose 6,7-dimethoxy-2,4-diaminoquinazolines of the formula

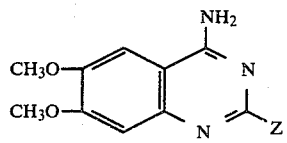

where Z is a nitrogen-containing heterocyclic group. One of these compounds, 2-[4-(2-furoyl)piperazin-1-yl]-4-amino-6,7-dimethoxyquinazoline, is a clinically useful antihypertensive agent and is marketed under the generic name "prazosin," the pharmacology of which is discussed in Constantine et al., "Hypertension: Mechanisms and Management," edited by Onesti, Kin and Moyer, Grune and Stratton, 1973, pp. 429–444.

U.S. Pat. Nos. 3,669,968 and 3,769,286 disclose 6,7,8-trialkoxy-2,4-diaminoquinazolines in which the 2-amino group is substituted by certain alkyl and hydroxy substituted alkyl groups or is a heterocyclic group such as piperidino or 4-substituted piperazino. One of these compounds is known by the generic name "trimazosin" and has the formula

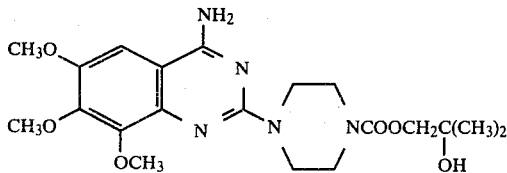

Trimazosin is also an active antihypertensive agent, see e.g., Vlachikis et al., *Current Therapeutic Research*, 17, 564 (1975). However, it is less potent than prazosin. Althuis et al., *J. Med. Chem.*, 20, 146 (1977) have shown the 6-0-demethyl derivative is a major metabolite of prazosin of considerably lower blood pressure lowering activity. The 7-0-demethyl derivative is a less prevalent metabolite.

U.S. Pat. Nos. 3,920,636 and 4,044,135 disclose homopiperazinoquinazoline compounds as antihypertensive agents.

Several patents have issued which disclose antihypertensive compounds of the general formula

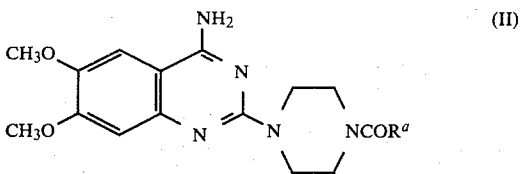

U.S. Pat. No. 4,001,237 claims compounds wherein $R^a$ is an oxazole, isoxazole, thiazole or isothiazole radical.

In U.S. Pat. No. 4,001,238, such compounds are disclosed wherein $R^a$ is of the formula

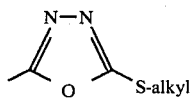

U.S. Pat. No. 3,780,040 discloses 3,4-dihydroquinazoline analogs of the above formula wherein $R^a$ is 2-thienyl.

In U.S. Pat. No. 4,026,894 and U.S. Pat. No. 4,112,097, $R^a$ is a 2-tetrahydrofuryl or 2-tetrahydropyranyl moiety. U.S. Pat. No. 4,060,615 claims compounds in which $R^a$ is cycloalkyl having 3 to 8 carbon atoms and cycloalkenyl having 4 to 8 carbon atoms. U.S. Pat. No. 4,101,548 is concerned with 1,2,3-thiadiazole amides of the above formula wherein $R^a$ is

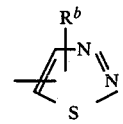

and $R^b$ is hydrogen, lower alkyl, $NH_2$ or $NHCO_2R^c$ $L$ in which $R^c$ is lower alkyl.

6,7-Dimethoxy-2-(4-thiomorpholin-1-yl) 4-aminoquinazolines and derivatives in which the 2-substituent is

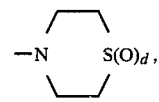

are disclosed as antihypertensive agents in U.S. Pat. No. 4,115,565.

British Pat. No. 1,530,768 discloses prazosin analogs in which the 2-amino group is of the formula

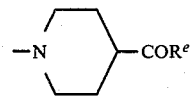

where $R^e$ is phenyl, substituted phenyl, furyl, thienyl or 5-alkylthio-1,3,4-oxadiazol-2-yl.

French Pat. No. 2,321,890 discloses analogs of prazosin in which the 2-amino substituent is a piperidino or piperazino group substituted in the 3 or 4 position.

The compounds of the invention are highly potent antihypertensive agents having improved duration of action since they are not susceptible to metabolic demethylation at the 6-position with resultant loss of activity as is the case with prazosin. In addition, the invention compounds have improved water solubility when compared to prazosin. They can therefore be administered intraveneously, particularly for emergency purposes and are uniformly absorbed by all patients.

SUMMARY OF THE INVENTION

The present invention discloses new 2,4-diaminoquinazoline compounds and processes for their production. The new 2,4-diaminoquinazolines possess valuable pharmacological properties and other aspects of the invention relate to pharmaceutical compositions for oral or parenteral administration to a mammal comprising one or more of said new compounds and a pharmaceutically acceptable carrier, as well as a method for treating hypertension which comprises orally or parenterally administering to mammals in need of such treatment an antihypertensive effective amount of a compound of the invention.

The compounds of the invention are also useful for their vasodilation properties, as antiglaucoma agents and in the treatment of congestive heart failure.

The novel compounds disclosed are of the formula (I)

wherein
$Y^1$ is hydrogen or chloro, $Y^2$ is OR and $Y^3$ is hydrogen or OR such that when $Y^1$ is hydrogen, $Y^3$ is OR and when $Y^1$ is chloro, $Y^3$ is hydrogen or OR, and the pharmaceutically acceptable acid addition salts thereof;
R is alkyl having from one to three carbon atoms;
$R^1$ and $R^2$ are the same or different and when taken separately are each a member selected from the group consisting of hydrogen, alkyl having from 1 to 5 carbon atoms, cycloalkyl having from 3 to 8 carbon atoms; alkenyl having from 3 to 5 carbon atoms, alkynyl having from 3 to 5 carbon atoms, hydroxy substituted alkyl having from 2 to 5 carbon atoms and when taken together with the nitrogen atom to which they are attached $R^1$ and $R^2$ form where
$X^1$ is a member selected from the group consisting of $S(O)_t$, $CHOR^6$, $-(CH_2)_p-$ and $CHR^7$, and $X^2$ is a member selected from the group consisting of $X^1$, O, $NR^3$, $NCOR^4$ and $NCOOR^5$, where
m is 2 or 3,
n is 2 or 3,
p is 1 to 3,
t is 0, 1 or 2;
$R^3$ is a member selected from the group consisting of hydrogen, alkyl having from 1 to 6 carbon atoms, alkenyl from 3 to 5 carbon atoms, alkynyl having from 3 to 5 carbon atoms, hydroxy substituted alkyl having from 2 to 5 carbon atoms, cycloalkyl having from 3 to 8 carbon atoms, $-(CH_2)_qC_6H_4R^8$ and $-(CH_2)_qC_{10}H_6R^8$ where q is 0 or 1;
$R^4$ is a member selected from the group consisting of hydrogen, alkyl having from 1 to 6 carbon atoms, alkenyl having from 3 to 5 carbon atoms, cycloalkyl and cycloalkylmethyl wherein said cycloalkyl has from 3 to 8 carbon atoms, $R^{10}$, $CH_2R^{10}$ and $(CH_2)_qC_6H_4R^8$ where A is S or O, q as defined above and $R^{10}$ is a member selected from the group consisting of where r is 1 or 2;
$R^5$ is a member selected from the group consisting of alkyl having from 1 to 7 carbon atoms, alkenyl having 3 to 5 carbon atoms, cycloalkyl having from 3 to 8 carbon atoms, hydroxy substituted alkyl having from 2 to 5 carbon atoms, $CH_2C_6H_4R^8$, $CH_2C_{10}H_6R^8$, $CH_2R^{10}$ and $CH_2O$-pyridyl;
$R^6$ is a member selected from the group consisting of hydrogen, $C_6H_4R^8$, $-(CH_2)_pZR^{15}$, alkyl having from 1 to 6 carbon atoms, and said alkyl substituted by a member selected from the group consisting of Cl, F, Br, OH, $CH_3O$, $SO_2CH_3$ and $NHSO_2CH_3$, where p and A are as previously defined and Z is a member selected from the group consisting of O, S, SO, $SO_2$, NH and $NR^{16}$;
$R^7$ is a member selected from the group consisting of alkyl having from one to six carbon atoms, hydroxyalkyl having from one to five carbon atoms, $-(CH_2)_qC_6H_4R^8$ and $COC_6H_4R^8$;
$R^8$ is a member selected from the group consisting of H, Cl, Br, F, $CH_3$, $CH_3O$, $CF_3$, OH, $SO_2CH_3$ and $NHSO_2CH_3$;
$R^9$ is a member selected from the group consisting of H, Cl, $CH_3$, $C_2H_5$ and phenyl;
$R^{11}$ is hydrogen or methylthio and
$R^{12}$ is a member selected from the group consisting of H, $NH_2$ alkyl having from one to four carbon atoms and $NHCO_2R^{14}$;
$R^{14}$ is alkyl having from one to four carbon atoms;
$R^{15}$ is a member selected from the group consisting of alkyl having from one to four carbon atoms, $C_6H_4R^8$ and $C_{10}H_6R^8$; and $R^{16}$ is hydrogen or alkyl having from one to four carbon atoms.

Preferred compounds of the invention include the compounds of formula (I) wherein $Y^1$, $Y^2$ and $Y^3$ are as defined above and $NR^1R^2$ is

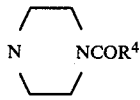

where $R^4$ is a member selected from the group consisting of

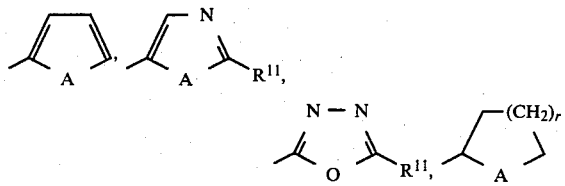

and cycloalkyl having from 3 to 8 carbon atoms and A, r and $R^{11}$ are as previously defined. Also preferred are the compounds of formula (I) wherein $Y^1$, $Y^2$ and $Y^3$ are as defined above and $NR^1R^2$ is

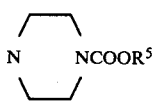

where $R^5$ is hydroxy substituted alkyl having from 2 to 5 carbon atoms.

Particularly preferred compounds of the invention are:

2-[4-(2-furoyl)piperazin-1-yl]-4-amino-7,8-dimethoxyquinazoline,

2-[4-(2-furoyl)piperazin-1-yl]-4-amino-6-chloro-7-methoxyquinazoline,

2-[4-(2-furoyl)piperazin-1-yl]-4-amino-6-chloro-7,8-dimethoxyquinazoline,

2-[4-(2-hydroxy-2-methylprop-1-yloxycarbonyl)piperazin-1-yl]-4-amino-7,8-dimethoxyquinazoline, 2-[4-(2-hydroxy-2-methylprop-1-yloxycarbonyl)piperazin-1-yl]-4-amino-6-chloro-7-methoxyquinazoline and 2-[4-(2-hydroxy-2-methylprop-1-yloxycarbonyl)piperazin-1-yl]-4-amino-6-chloro-7,8-dimethoxyquinazoline, and their hydrochloride salts.

The invention further provides certain intermediates useful in the preparation of the compounds of formula (I). These intermediates are of the formula

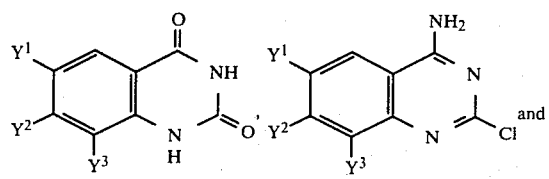

and

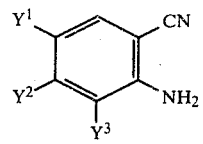

where $Y^1$, $Y^2$ and $Y^3$ are as defined above.

The term "pharmaceutically acceptable" used herein to describe an acid addition salt of a compound of formula (I) refers to those salts having anionic species of a variety of relatively non-toxic inorganic or organic acids. The anion does not contribute appreciably to the toxicity of the salt or to its pharmacological activity. Illustrative of such salts are those formed with acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids. Preparation of the mono-acid addition salts may be carried out in conventional manner by treating a solution or suspension of the free base in a reaction inert organic solvent with one chemical equivalent of the acid or if the di-acid addition salt is desired, at least two chemical equivalents of the acid. Conventional concentration or crystallization techniques are employed in isolating the salts.

The compounds of formula (I) are especially useful as antihypertensive agents having significant advantages over the prior art. The $Y^1$ substituent, at the 6-position of the invention compounds, is either hydrogen or chloro, groups which are not prone to metabolic attack. Consequently, the invention compounds are not subject to facile metabolic demethylation with resultant loss of activity, as has been shown for prazosin. Accordingly, the compounds of formula (I) have greater duration of action than prazosin and other 6,7-dimethoxy- and 6,7,8-trimethoxyquinazoline antihypertensive agents known in the art.

The invention compounds also have significantly greater water solubility than prazosin and as a result of their improved solubility, are uniformly absorbed by all patients. Furthermore, they can be administered in time release form, as well as parenterally, including intravenously.

DETAILED DESCRIPTION OF THE INVENTION

The antihypertensive compounds of the invention are represented by either of the formulae

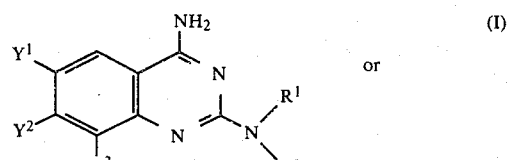

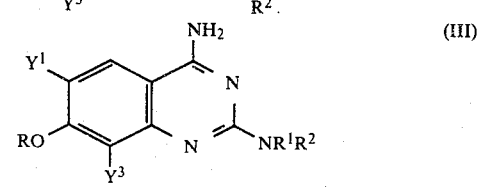

wherein $Y^1$, $Y^2$, $Y^3$, R, $R^1$ and $R^2$ are as previously defined. They are prepared by synthetic methods described below.

Scheme I, below, outlines a preferred reaction sequence. In the first step a 4-alkoxyanthranilic acid of formula (IX) containing the desired substituents $Y^1$ and $Y^3$ as defined above is cyclized to the corresponding 2,4-dioxoquinazoline of formula (X). The cyclization is brought about by reacting the compound (IX) with sodium or potassium cyanate or urea according to the procedure of Curd et al., *Jour. Chem. Soc.*, 777 (1947) for the corresponding 6,7-dimethoxyquinazolinediones. Of course, as will be apparent to one skilled in the art, the anthranilic acids of formula (IX) may be replaced in this reaction by the corresponding compounds in which the carboxylic acid moiety is replaced by a $CONH_2$, CN, or carboxylic ester group with satisfactory results. The cyclized compounds of formula (X) are novel compounds, of value as intermediates for preparing the antihypertensive compounds of the invention. As will be recognized by one skilled in the art, they may also be represented as the corresponding tautomeric 2,4-dihydroxyquinazolines.

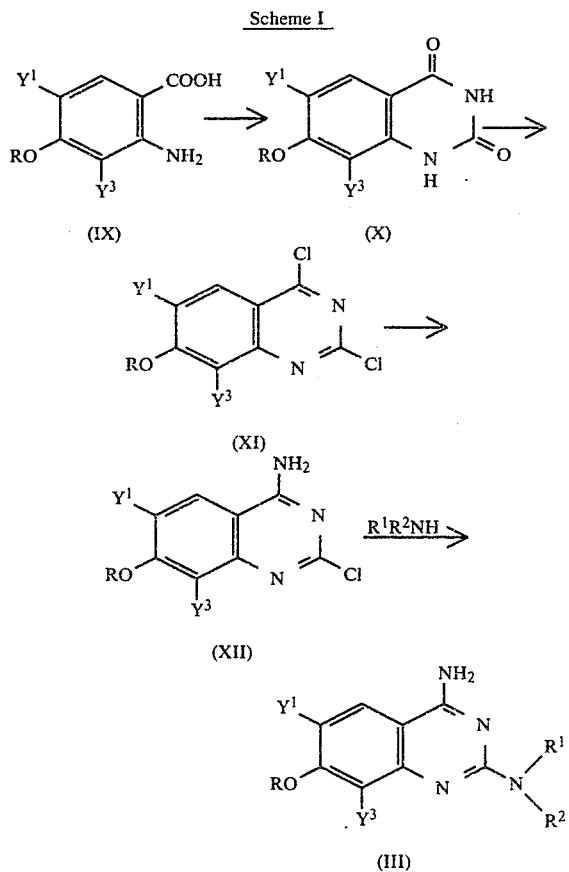

Scheme I

In preparing the intermediates of formula (X), the starting material (IX) is suspended in a polar solvent in the presence of acid, preferably water-acetic acid, and a 2-4 molar excess of the cyanate salt, e.g., potassium cyanate or urea added. The resulting mixture is then heated at a temperature of from about room temperature up to the reflux temperature of the solvent until reaction is substantially complete. Typical reaction times are from about 1 to 24 hours. The mixture is then cooled, made alkaline with sodium hydroxide or potassium hydroxide and the alkaline mixture heated again at a temperature of from about 70° to 100° C. for 1 to 5 hours. The resulting sodium salt of the product (X) is then acidified and isolated by standard methods known in the art.

The intermediate of formula (X) is then reacted with a mixture of phosphorous pentachloride and phosphorous oxychloride or the corresponding phosphorous bromides to prepare the corresponding 2,4-dihaloquinazolines. The preferred embodiment, in which the above phosphorous chlorides are employed, is depicted in Scheme I to provide the intermediates of formula (XI) in which R, $Y^1$ and $Y^3$ are as defined above. Typically the dione (X) and a 2 to 4 molar excess each of phosphorous pentachloride and phosphorous oxychloride are heated at reflux for 2 to 6 hours, the residual phosphorous oxychloride evaporated and the residue slurried in a reaction inert organic solvent, for example, chloroform or dichloromethane, and poured into ice-water. Insoluble material is removed and the product isolated from the organic layer by evaporation or precipitation by addition of a non-solvent, for example, hexane, to precipitate the dichloro compound of formula (XI).

The key 2-chloro-4-aminoquinazoline intermediates of formula (XII) are provided by reacting equimolar amounts of ammonia and 2,4-dichloroquinazoline (XI) in the presence of a reaction inert organic solvent. Examples of suitable reaction inert solvents are ethyl ether, tetrahydrofuran, chloroform and benzene. A preferred solvent is tetrahydrofuran. In ordinary practice a preferred excess of ammonia of from one to ten moles would be used in order to shift the reaction toward completion. The temperature at which this reaction can be carried out is from about 25° to 200° C. for a period of from one to 48 hours. A preferred reaction temperature and time for this reaction would be about 25° to 60° C. for about five hours. Upon completion of the reaction the product is recovered by conventional means. For instance, the solvent can be evaporated and the crude solid can be triturated with water or precipitated from dilute aqueous acid in crystalline form and subsequently recrystallized from any number of organic solvents such as methanol, dimethylformamide or their mixtures with water.

Conversion of the 2-chloroquinazoline intermediate of formula (XII) to the desired compound of formula (III) is accomplished by contacting the intermediate (XII) with an equimolar amount of an amine of the formula $R^1R^2NH$ in the presence of an aqueous or an organic solvent. A small molar excess of amine is generally employed. Preferred organic solvents for this reaction include polar solvents like tetrahydrofuran, dioxane, dimethylacetamide, dimethylformamide; alcohols such as methanol, ethanol and isoamyl alcohol and ketones such as methylethylketone and methylisobutylketone. Particularly preferred solvents are isoamyl alcohol and methylisobutylketone. The reaction mixture is heated preferably at a temperature of from about 60° to 160° C. for from one to 65 hours. Particularly preferred reaction temperatures are from about 100° to 140° C. and temperatures in this range are conveniently obtained by maintaining the reaction mixture at the reflux temperature of the particularly preferred solvents. At such temperature the reaction is ordinarily complete in from about two hours to two days.

Alternate procedures for preparing the compounds of the invention may also be used with satisfactory results. For example, the alternate methods disclosed in U.S. Pat. No. 3,511,836 for preparation of prazosin and its analogs can also be used with the appropriate starting materials to provide the invention compounds of formula (I). These methods are enumerated and discussed briefly below.

1. 2-Amino-4-chloroquinazolines (XXIX) prepared by methods analogous to those described in U.S. Pat. No. 3,511,836 for the corresponding 6,7-dialkoxy-compounds may be reacted with ammonia under conditions described above for the conversion of compounds (XI) to (XII) with resultant formation of the desired product of formula (I) where $Y^1$, $Y^2$ $Y^3$, $R^1$ and $R^2$ are as defined above.

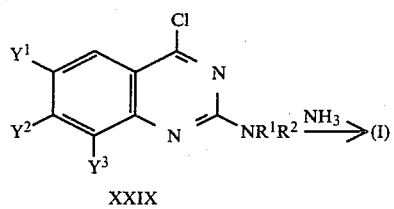

XXIX

2. The quinazolinedione of formula (X) can be reacted with a reagent such as phosphorous pentasulfide or the like to form the corresponding 2,4-quinazolinedithione which are in turn reacted with an alkyl or benzyl halide to form the corresponding 2,4-dithioalkylquinazoline or 2,4-dithiobenzylquinazoline. This is then reacted with ammonia by the procedure previously described for the reaction of the 2,4-dichloroquinazolines (XI) to provide the corresponding 4-amino-2-thioalkyl (or thiobenzyl) quinazoline (XX). The latter compound is then converted to the desired compound (I) by employing conditions previously described for the formation of compound (I) from 2-chloro compounds of formula (XII).

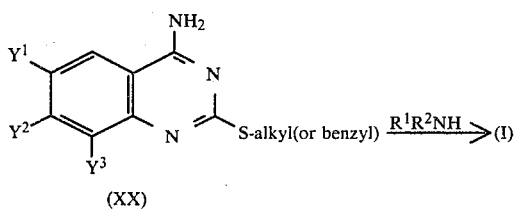

(XX)

where $Y^1$, $Y^2$, $Y^3$, $R^1$ and $R^2$ are as previously defined.

3. Compounds of formula (I) wherein $NR^1R^2$ forms a heterocyclic moiety of the formula

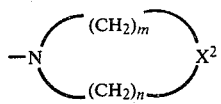

where $X^2$ is $NR^3$, $NCOR^4$ or $NCOOR^5$ and m, n, $R^3$, $R^4$ and $R^5$ are as previously defined, but $R^3$ is other than hydrogen, can also be prepared from the compound wherein $X^2$ is NH, for example $NR^1R^2$ is piperazino, by acylation, alkylation or carbonyloxylation.

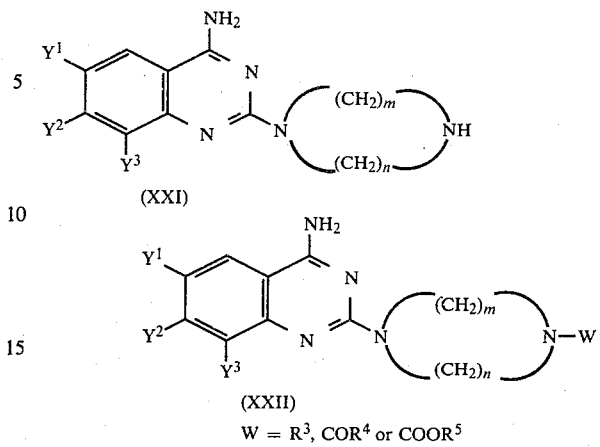

$W = R^3$, $COR^4$ or $COOR^5$

The compound (XXI) is reacted with a compound of formula $R^3—X^3$, $R^4COX^3$ or $X^3COOR^5$, where $R^3$, $R^4$ and $R^5$ are as defined above and $X^3$ is a leaving group, preferably the halides, Cl or Br. When the preferred halides are employed it is advantageous to use at least a slight molar excess to ensure complete reaction. The intermediate (XXI) and reagnet of formula $R^3X^3$, $R^4COX^3$ or $X^3COOR^5$ are contacted in the presence of a reaction inert organic solvent, for example, benzene, tetrahydrofuran, acetone methylethyl ketone, methylisobutyl ketone, 1,2-dimethoxyethane or diethyleneglycol dimethylether. A preferred such solvent is methylisobutyl ketone. The reaction may be carried out successfully over a wide range of temperatures. However, a temperature in the range of about 0° C. up to the reflux temperature of the solvent is preferred for reasons of efficiency and convenience. At such a preferred temperature the reaction is ordinarily complete in from about 30 minutes to six hours. The resulting solid product is then isolated as either the hydrohalide or the free base by conventional methods and purified, if desired, by crystallization, column chromatography or the like.

4. In this method the 2-aminobenzonitrile intermediate of formula (XIV) is reacted with a guanidine of the formula

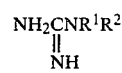

where $R^1$ and $R^2$ are as defined above. The benzonitrile (XIV) and an equivalent amount, but preferably a molar excess, of the guanidine are contacted in the presence of a reaction inert organic solvent, for example, ethylene glycol, diethyleneglycol, dimethylformamide, dimethylsulfoxide or diethyleneglycol dimethylether, at a temperature of from about 120°–180° C. for from about four to 15 hours. The desired product of formula (I) is then isolated by well known methods, for example, the solvent is evaporated, the residue contacted with water and the precipitated product is filtered, recrystallized and dried. The reaction is illustrated as follows:

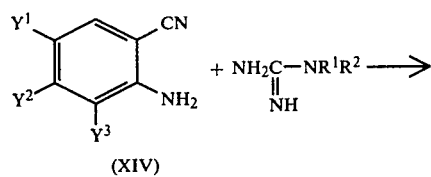

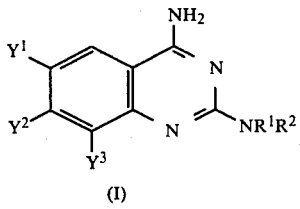

(XIV)

(I)

The guanidine starting materials are prepared by methods well known in the art. For example, the amine of formula $R^1R^2NH$ is reacted with cyanogen bromide to form the corresponding N-cyano-compound which, in turn, is reacted with hydroxylamine, followed by catalytic hydrogenation using the methods and conditions of Carrington, *Jour. Chem. Soc., London*, 2527 (1955) for the conversion of anthranilonitrile into 2-aminobenzamidine.

Variations of the above method can also be carried out employing either of the following starting materials in place of the 2-aminobenzonitrile (XIV).

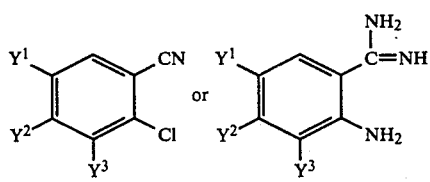

The 2-chlorobenzonitriles are obtained, for example, by diazotization of (XIV) in the presence of cuprous chloride. The 2-aminobenzamidines are obtained, for example, by the method of Carrington, above.

5. Chloro-4-alkoxy-7,8-disubstituted quinazolines, which are prepared by methods described by Curd et al., *Jour. Chem. Soc.*, 775 (1974) for the isomeric 2-chloro-4-alkoxy-6,7-disubstituted quinazolines, can be reacted with an amine, $R^1R^2NH$, to obtain the corresponding 2-aminoquinazolines. The 4-alkoxy substituent is then replaced by $NH_2$ by reaction with ammonia as described above for the 4-chloro compounds of formula (XXIX). This reaction sequence is exemplified below for a 2-chloro-4-ethoxyquinazoline starting material.

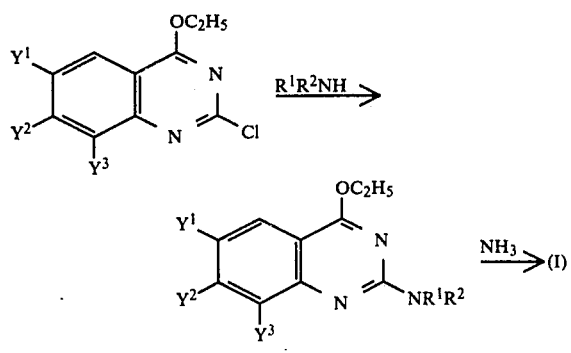

$Y^1$, $Y^2$, $Y^3$, $R^1$ and $R^2$ are as previously defined. The 4-thioalkylquinazolines corresponding to the above 4-alkoxy compounds can also be employed as starting materials in this sequence.

6. The compounds of the invention are also provided by methods disclosed in U.S. Pat. No. 3,935,213 for prazosin, trimazosin and analogs thereof as set forth below where $Y^1$, $Y^2$, $Y^3$, $R^1$ and $R^2$ are as previously defined;

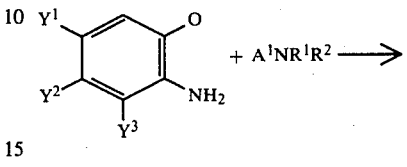

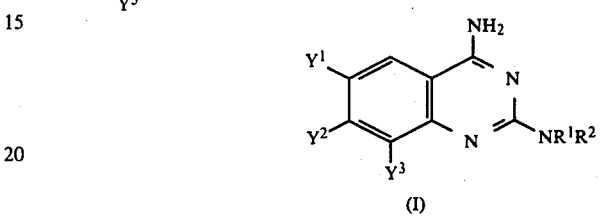

(I)

$A^1$ is selected from the group consisting of CN and $C(=NH)XR_3$ wherein X is O or S and $R_3$ is alkyl having from one to six carbon atoms; and Q is CN or $-C(=NH)NH_2$. Preferably the reaction is carried out in the presence of from about 0.5 to 5 molar equivalents of a basic catalyst, e.g., sodium hydride, potassium ethoxide or triethylamine, and at a temperature in the range of from about 50° to 180° C. The products of formula (I) are isolated by well known methods, for example, those described in U.S. Pat. No. 3,935,213.

7. Compounds of formula (I) are also obtained by employing the appropriate starting material of formula (XIV) in the process described in Belgian Pat. No. 861,821 and 861,822 for synthesis of prazosin. The method is outlined in Scheme II. The o-aminobenzonitrile (XIV) wherein $Y^1$, $Y^2$ and $Y^3$ are as defined above is reacted with at least an equimolar amount of thiophosgene in a reaction inert organic solvent, e.g., 1,2-dichloroethane. To the mixture is added a base, e.g. calcium carbonate, water and the mixture stirred typically at about 0°–5° C., then warmed to about room temperature until reaction is substantially complete.

Scheme II

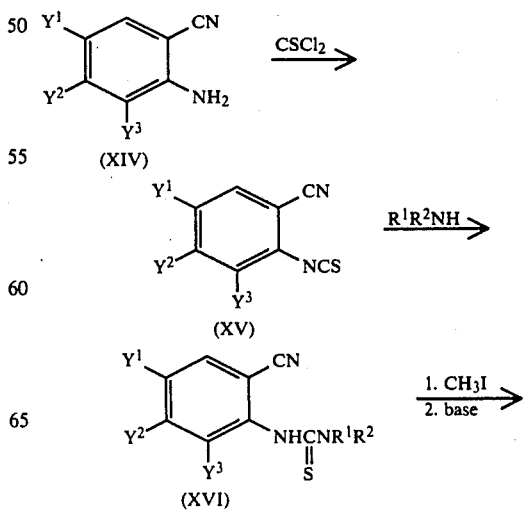

-continued
Scheme II

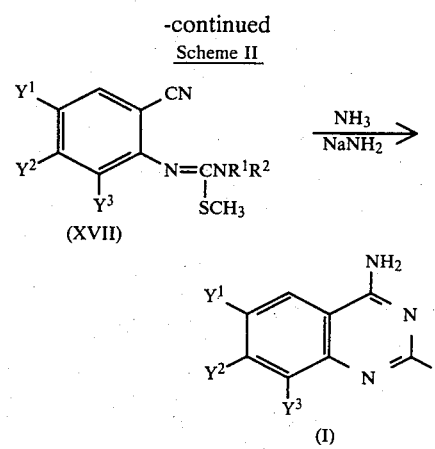

The o-isothiocyanatobenzonitrile (XV) produced is isolated in crude form for use in the next step. The intermediate (XV), dissolved in a reaction inert organic solvent, typically ethyl acetate, is contacted with the amine of formula $R^1R^2NH$, where $R^1$ and $R^2$ are as defined above, at a temperature below 0° C., preferably at about −30° to −5° C. to obtain the o-thioureidobenzonitrile (XVI). This is then contacted with a methylating agent, for example methyl iodide or methyl bromide, and the resulting S-methyl hydrohalide salt treated with a mild base to obtain the S-methylthioformamidate of formula (XVII) which is cyclized by reaction with anhydrous ammonia in the presence of a polar solvent and an alkali metal amide to provide the desired compounds of formula (I). Preferred polar solvents for the cyclization are formamide or N,N-dimethylformamide. Also preferred for the final step are use of from 1 to 3 equivalents of alkali metal amide, especially sodium amide and a temperature of from about 100° to 150° C.

8. In U.S. Pat. No. 4,138,561 a novel process for preparing prazosin and trimazosin is disclosed. This method is also suitable for preparation of the compounds of the present invention as shown below.

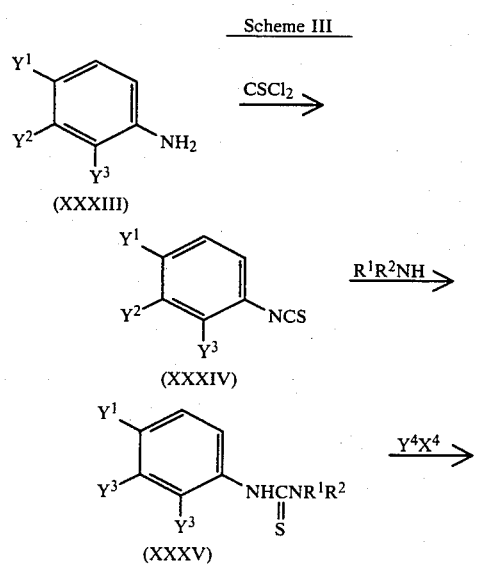

-continued
Scheme III

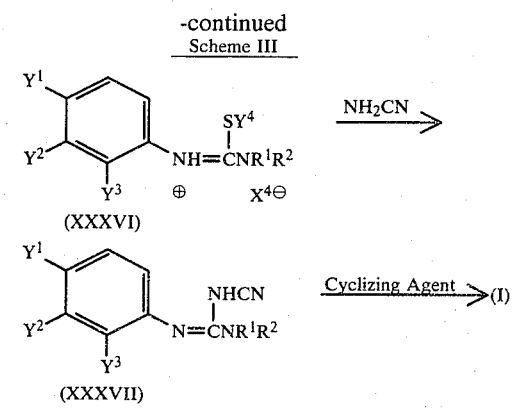

The starting materials of formula (XXXIII) wherein $Y^1$, $Y^2$ and $Y^3$ are as previously defined are known compounds [see, for example, Gibson et al., *J. Chem. Soc.*, 111, 79 (1917); Munavalli et al., *Bull. Soc. Chim., France*, 3311 (1966); *Chem. Abstr.*, 66, 46303s (1967); and German Offenlegungsschrift No. 1,959,577; *Chem. Abstr.*, 75, 63397d (1971)]. The starting material (XXXIII) is converted to the isothiocyanate (XXXIV) as described above for intermediate (XV) and this is reacted with an amine $R^1R^2NH$ wherein $R^1$ and $R^2$ are as defined above to provide the subsituted thiourea (XXXV) by the method described above for intermediate (XVI). The intermediate (XXXV), in turn, is reached with an alkylating agent, $Y^4X^4$ to obtain an intermediate of formula (XXXVI) in which $Y^4$ is alkyl having from one to four carbon atoms or an aryl derivative containing electron withdrawing groups, for example, 2,4-dinitrophenyl, and $X^4$ is a member selected from the group Cl, Br, I, alkyl-$SO_4$ having from one to four carbon atoms, $C_6H_5SO_2$, $F_3CSO_2$ and $FSO_3$. An especially preferred alkylating agent, $Y^4X^4$, is methyl iodide. Alternatively, as disclosed in U.S. 4,138,561, phosgene may be used in the first step in the above reaction sequence of Scheme III, wherein each of the intermediates (XXXIV) to (XXXVI) is the corresponding compound in which an atom of oxygen replaces the sulfur atom shown therein. The intermediate of formula (XXXVI) is then reacted with cyanamide to provide the corresponding carboxamidine intermediate of formula (XXXVII).

Alkylation of thiourea derivatives (XXXV) and subsequent reaction with cyanamide is normally carried out in a reaction inert organic solvent. Suitable solvents include dioxane, tetrahydrofuran, dimethyl sulfoxide, and the alkanols having from one to five carbon atoms. These reactions are preferably carried out at a temperature of from about 25° to 100° C. for a period of about 0.5 to 24 hours. The intermediate of formula (XXXVII) may also be obtained by alternate procedures described in U.S. Pat. No. 4,138,561.

The conversion of carboxamidine intermediates (XXXVII) to the desired quinazolines of formula (I) is carried out by reaction with cyclizing reagents such as phosphorus trichloride or phosphorus pentachloride in a solvent amount of phosphorus oxychloride. Other phosphorus halides and phosphorus oxyhalides such as phosphorus tribromide and phosphorus pentabromide in a solvent amount of phosphorus oxybromide may be employed. The ring closure may also be carried out by reacting the intermediate (XXXVII) with acidic reagents such as aqueous hydrogen chloride, hydrogen chloride in phosphorus oxychloride, trichloroacetic acid or Lewis acid catalysts such as $ZnCl_2$, $FeCl_3$, $AlCl_3$, $AlBr_3$, and the like.

With respect to carrying out the reaction with phosphorus halides, approximately equimolar amounts of the carboxamidine (XXXVII) and phosphorus halides are employed with convenient amount of phosphorus oxyhalide relative to the amount of starting material (XXXVII). The term "solvent amount" as used herein refers to a quantity of phosphorus oxychloride or phosphorus oxybromide sufficient to provide good mixing and handling characteristics with respect to the reaction mixtures. For this purpose a ratio of from about 2 to 15 ml. of the phosphorus oxyhalide for each gram of carboxamidine reactant of formula (XXXVII) is generally preferred.

Commonly used temperatures for carrying out the cyclization reaction range from about 25° to 125° C. with a preferred temperature of from about 70° to 100° C. As will be appreciated by those skilled in the art, reaction times and conditions required for cyclization of intermediates (XXXVII) to form the desired products of formula (I) vary according to several factors such as temperature and reaction time. For example, at lower temperatures, longer reaction periods are needed, while at higher temperatures, the cyclization reaction is completed in a shorter time. Reaction periods of from about 0.5 to 24 hours can be used, however a period of from about 1 to 3 hours is preferred at the above mentioned preferred reaction temperatures.

The required starting materials of formula (IX) for the procedure of Scheme I, above are obtained by the reaction sequences illustrated in Schemes IV, V and VI below, for the case where R is $CH_3$.

Scheme IV

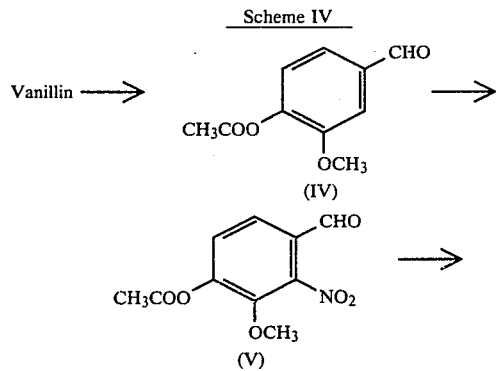

-continued
Scheme IV

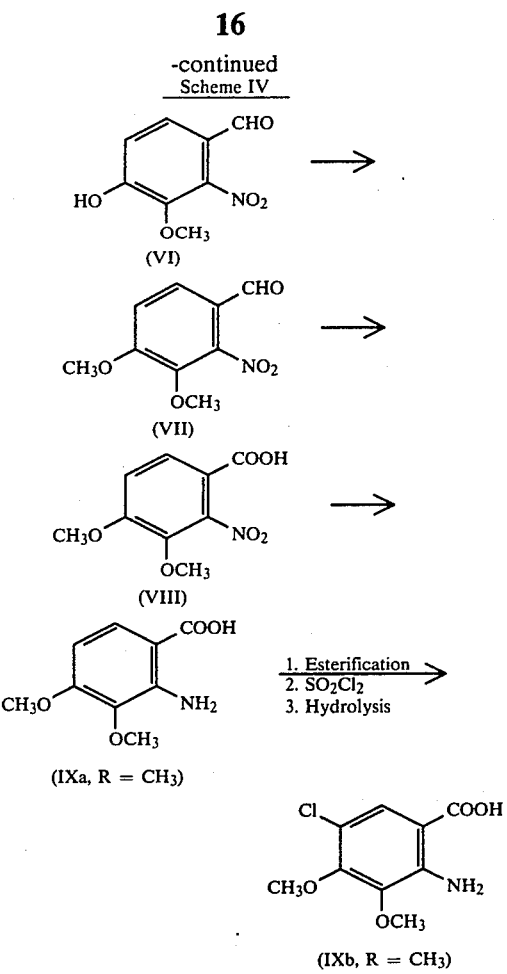

In the reaction schemes above and below, for the sake of convenience, the lower case letters a, b and c are used after the Roman numerals for the compounds shown to denote the following:

a. $Y^1=H$, $Y^2=Y^3=OR$ where R is alkyl having from one to three carbon atoms.
b. $Y^1=Cl$, $Y^2=Y^3=OR$, R is as defined above.
c. $Y^1=Cl$, $Y^2=OR$ as defined above, $Y^3=H$.

Scheme V

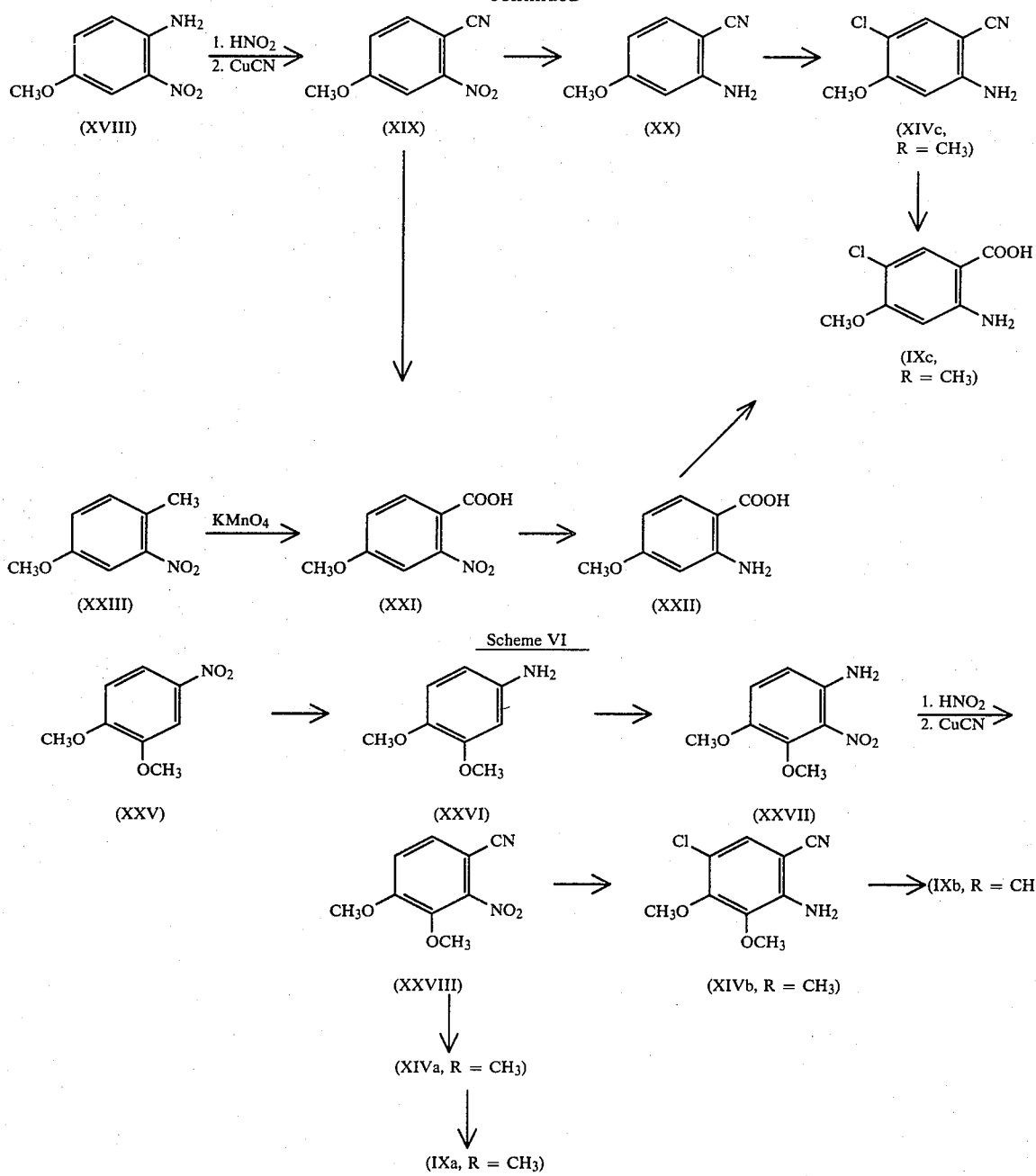

In the reaction sequence of Scheme IV vanillin is acetylated with, for example acetic anhydride or acetyl chloride by well known methods and the acetylated intermediate nitrated to obtain 4-acetoxy-3-methoxy-2-nitrobenzaldehyde (V). The acetyl group is removed by hydrolysis, for example by treatment with an aqueous strong base such as sodium hydroxide, followed by acidification to provide the 4-hydroxy-3-methoxy-2-nitrobenzaldehyde intermediate of formula (VI). This intermediate is then alkylated with one of the well known alkylating agents commonly employed for the conversion of phenolic groups to the corresponding alkyl ethers. Examples of such alkylating agents are dimethylsulfate, diethyl sulfate, methylbromide, n-propyl iodide and ethyl iodide. In the case illustrated in Scheme IV a methylating agent is employed to provide 3,4-dimethoxy-2-nitrobenzaldehyde, (VII). Compounds in which the two ether groups are different are obtained by use of, for example, diethyl sulfate or n-propyl iodide as the alkylating agent. When ethyl vanillin or n-propyl vanillin are employed in place of vanillin as starting material in this reaction sequence the corresponding compounds are likewise obtained wherein the corresponding alkoxy groups are 4,5-diethoxy, 4,5-dipropoxy, 4-ethoxy-5-methoxy, 4-ethoxy-5-n-propoxy, 4-n-proproxy-5-methoxy and 4-n-propoxy-5-ethoxy.

The dialkoxy intermediate of formula VII, e.g., is then oxidized to the corresponding carboxylic acid. While a wide variety of oxidizing agents and conditions are known in the art to bring about oxidation of aromatic aldehydes to the corresponding carboxylic acids, preferred oxidizing conditions are those employing potassium permanganate in aqueous acetone at the reflux temperature of the mixture. The 2-nitro-4,5-dialkoxy-benzoic acid intermediate, e.g. the compound of formula (VIII) is isolated by known means and reduced to the corresponding 2-amino acid, for example, the compound of formula (IXa, R=CH$_3$), by well known means, e.g. by catalytic hydrogenation employing a noble metal hydrogenation catalyst. A preferred catalyst is palladium.

The intermediate of formula (IXa) is useful as a starting material in the reaction sequence shown in Scheme I, above, to provide the corresponding invention compounds of formula (Ia) or (IIIa). Alternatively, as shown in Scheme IV, the intermediates (IXa) serve as a starting material for the corresponding 5-chloro intermediates of formula (IXb). The carboxylic acid is first esterified to form an alkyl ester, e.g. the methyl or ethyl ester, by well known means. The ester is then chlorinated employing, for example chlorine or sulfuryl chloride and the latter reagent is preferred for reasons of efficiency and ease of handling. Typically a slight molar excess, e.g. a 20% molar excess, of sulfuryl chloride is added to a cooled solution of the intermediate carboxylate ester of the acid (IXa) in a chlorinated hydrocarbon solvent, e.g. chloroform, methylene chloride or 1,2-dichloroethane, the resulting mixture is allowed to warm to room temperature, then heated at reflux until reaction is substantially complete, e.g. from one hour to 24 hours. The crude 5-chloro ester is then hydrolyzed, e.g. by means of sodium hydroxide as described above to provide the corresponding 5-chloro acid of formula (IXb).

The starting 5-chloro-5-alkoxyanthranilic acids of formula (IXc) are obtained as shown in Scheme V. 4-Methoxy-2-nitroaniline (XVIII) is treated with sodium nitrite in concentrated hydrochloric acid under conditions well known to those skilled in the art, to form an intermediate diazonium salt to which is then added an aqueous solution containing an equimolar amount of cuprous cyanide and a molar excess, typically a 50% excess, of potassium cyanide while warming the reaction mixture on a steam bath. The product 4-cyano-3-nitroanisole (XIX) is then isolated and then hydrolyzed, e.g. in the presence of aqueous sulfuric or hydrochloric acid to obtain the carboxylic acid of formula (XXI). This, in turn, is hydrogenated as described above for the conversion of compound (VIII) to (IXa) to provide 4-methoxy anthranilic acid (XXII) and the latter chlorinated to provide the desired compound (IXc, R=CH$_3$) employing the conditions described above for the conversion of compounds of formula (IXa) to 5-chloro compounds (IXb).

As shown in Scheme V, other synthetic routes may be employed to provide the desired starting material of formula (IXc). In one such alternate method the 4-cyano-3-nitroanisole (XIX) is hydrogenated as previously defined for conversion of compound (VIII) to compound (IXa) to provide the aminonitrile of formula (XX). This is chlorinated as described above for the conversion of compounds (IXa) to (IXb) and the resulting 5-chloro nitrile (XIVc, R=CH$_3$ ) is hydrolyzed as described for the preparation of compound (XXI) from nitrile (XIX), to provide the desired compound (IXc, R=CH$_3$).

Another route shown in Scheme V involves oxidation of the starting material 4-methyl-3-nitroanisole with potassium permanganate to provide the intermediate (XXI) which is converted to compound (IXc) as previously described.

As will be obvious to those skilled in the art when the methoxy group present in the starting materials of formula (XVIII) and (XXIII) employed in Scheme V is replaced by an ethoxy or n-propoxy group, the corresponding compounds of formula (IXc) are obtained wherein R is C$_2$H$_5$ or n-C$_3$H$_7$, respectively.

Similarly, replacement of either one or both of the methoxy groups present in the starting material of formula (XXV) employed in Scheme VI by ethoxy or n-propoxy provides the corresponding compounds of formula (IXa) or (IXb).

The starting materials of formula (XIV) employed in the reaction sequence illustrated in Scheme II for the preparation of the compounds of the invention, are prepared as shown in Scheme V for compounds (XIVc) and in Scheme VI for compounds (XIVa) and (XIVb), and as described above.

Many of the requisite amines of formula R$^1$R$^2$NH wherein R$^1$ and R$^2$ are as previously defined are known compounds, see for example, the references mentioned above as prior art. Those that are new are prepared by methods which will be apparent to those skilled in the art. For example, the amines of formula

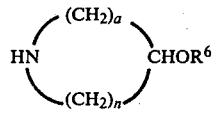

where a is 1, 2, or 3, n is 2,. or 3 and R$^6$ is as defined above are obtained by reacting the appropriate corresponding N-protected amine wherein R$^6$ is hydrogen with, for example, a compound of the formula (R$_6$)'-Hal where (R$^6$)' has any of the values assigned above for R$^6$ except hydrogen and Hal is Cl, Br, I or other known leaving groups such as SO$_3$CH$_3$. The reaction is typically carried out employing an equimolar amount of a metal hydride, for example sodium hydride and in the presence of a reaction inert organic solvent, e.g. dimethylformamide. The N-protecting group is then removed to provide the desired amine of the above formula. Typically, protecting groups such as acetyl or benzyl are employed. The former being removed by hydrolysis and the latter by catalytic hydrogenation, e.g., employing a palladium catalyst.

Alternatively, the above compounds wherein R$^6$ contains an ether moiety can be obtained by the reaction sequence below which illustrates the preparation of 4-(ethoxy-n-propoxy)piperidine.

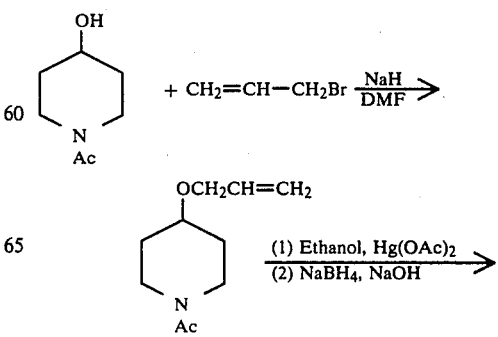

-continued

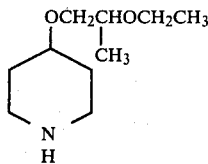

Many of the requisite amines of formula

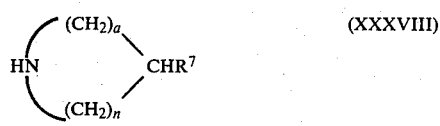

(XXXVIII)

wherein a, n and $R^7$ are as defined above are known compounds. Those that are not known are prepared by well known methods. For example, the $R^7$-substituted piperidines may be obtained by catalytic hydrogenation of the corresponding $R^7$-substituted pyridines. The cyclic amines of the above formula wherein $R^7$ is alkyl having from one to six carbon atoms are provided by reacting the appropriate N-protected aminoketone with an alkyl Grignard reagent, for example, as outlined below.

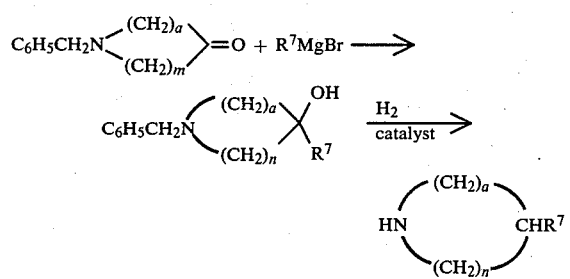

The catalytic hydrogenolysis of the tertiary hydroxy group is often facilitated by prior acetylation.

The desired cyclic amines wherein $R^7$ is hydroxyalkyl having from two to five carbon atoms are obtained, for example by methods outlined below.

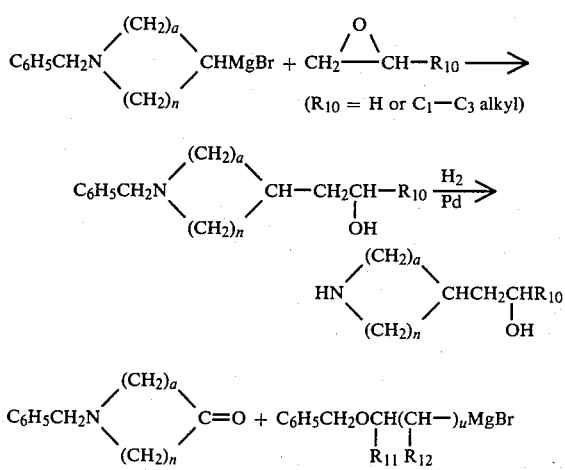

$R_{11}$ and $R_{12}$ are each H or alkyl of 1 to 3 carbon atoms, u is 1 to 4

-continued

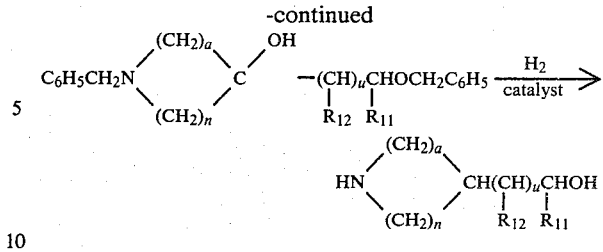

The compounds of formula (XXXVIII) wherein $R^7$ is hydroxymethyl are obtained by e.g. lithium aluminum hydride reduction of the corresponding aldehydes or carboxylic acid esters.

The compounds of formula (XXXVIII) wherein $R^7$ is $R^8C_6H_4(CH_2)_8$ wherein q is 0 or 1 and $R^8$ is as previously defined may also be obtained via a Grignard reaction as shown below, for example.

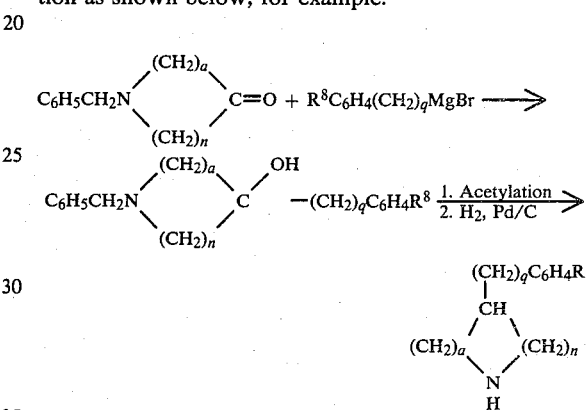

The starting materials of formula (XXXVIII) wherein $R^7$ is $R^8C_6H_4CO$ may be obtained, for example, by Friedel-Crafts acylation of $R^8C_6H_5$ by an N-protected carboxylic acid halide as illustrated below.

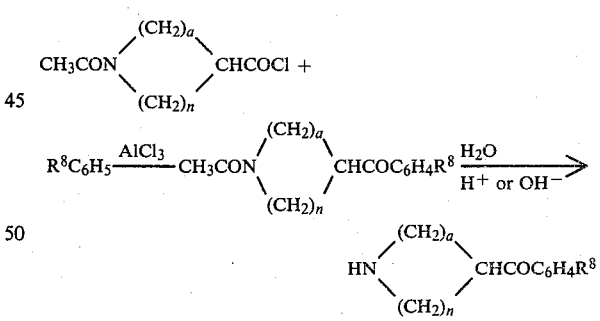

The piperidine derivatives of the latter formula are also obtained by employing the corresponding pyridine carboxylic acid halides and compound of formula $R^8C_6H_5$ in the Friedel-Crafts acylation followed by hydrogenation of the pyridine moiety.

The cyclic aminocarboxylic acid precursors of the above N-protected cyclic aminoacid halides are either readily available or may be obtained by the well known Dieckmann reaction followed by hydrolysis and decarboxylation of the resulting alpha-ketoester to provide a cyclic ketone intermediate which can be converted to the desired carboxylic acid by a variety of methods, e.g.

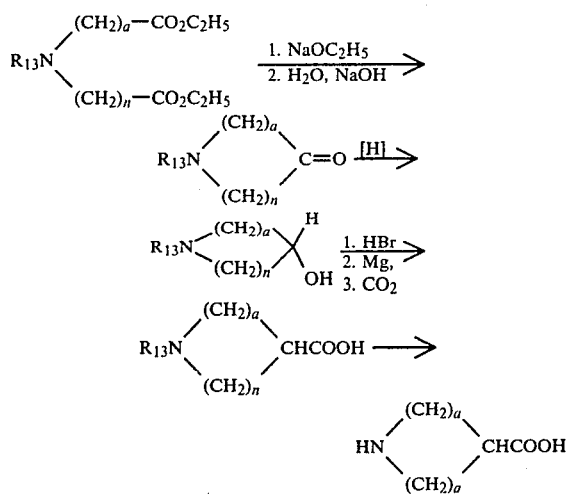

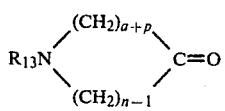

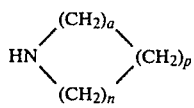

In the above reaction sequence a and n are as defined above and $R_{13}$ is a suitable amino protecting group, e.g. benzyl or acetyl. As will be recognized by one skilled in the art, in the above reaction sequence when $R_{13}$ is benzyl the ketone reduction step is preferably carried out by a metal hydride, e.g. sodium borohydride or lithium aluminum hydride, and removal of the benzyl group is accomplished by hydrogenolysis.

Use of a longer chain $R_{13}$-protected iminodicarboxylate esters in the above Dieckmann reaction can be employed to provide the corresponding $R_{13}$-protected amino ketones of the formula $$R_{13}N \underset{(CH_2)_{n-1}}{\overset{(CH_2)_{a+p}}{\diagup\!\!\!\diagdown}} C=O$$

which upon Wolff-Kishner reduction and deprotection provides starting materials of formula $$HN \underset{(CH_2)_n}{\overset{(CH_2)_a}{\diagup\!\!\!\diagdown}} (CH_2)_p$$

where a, n and p are as defined above.

The antihypertensive activity of the compounds of the invention is shown by their ability to lower the blood pressure of conscious spontaneously hypertensive rats and conscious renally hypertensive dogs, when administered orally at doses of up to 30 mg./kg.

For instance, 2-[4-(2-hydroxy-2-methylprop-1-yloxycarbonyl)piperazin-1-yl]-4-amino-6-chloro-7,8-dimethoxyquinazoline, a typical and preferred compound of the invention, has been found to lower blood pressure in renally hypertensive dogs to a statistically significant degree, e.g., when this compound is administered orally at doses as low as 0.2 mg./kg., it effected a decrease of 30 mm. Hg after 4 hours with no significant change in heart rate or other side effect. Similarly, at the same dosage 2-[4-(2-hydroxy-2-methylprop-1-yloxycarbonyl)piperazin-1-yl]-4-amino-6-chloro-7-methoxyquinazoline, a particularly preferred compound of the invention, caused a reduction of 40 mm. Hg after one hour which increased only by 20 mm. Hg 6 hours after administration; and another particularly preferred compound: 2-[4-(2-furoyl)-1-piperazinyl]-4-amino-6-chloro-7-methoxyquinazoline effected a reduction in blood pressure of 40 mm. Hg which increased by only 5 mm. Hg six hours after the oral dose (0.2 mg./hg.) had been administered. Again, no significant heart rate change or other unwanted side effect was noted with the latter two compounds.

In addition to their useful antihypertensive activity, the compounds of the invention also demonstrate activity in standard tests designed to show vasodilator activity, antiglaucoma activity and utility in the treatment of congestive heart failure.

The compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic. For treatment of glaucoma, they can be administered topically as well as by the above mentioned routes of administration. For topical application, a compound of the invention is admixed under sterile conditions with a pharmaceutically-acceptable liquid carrier or solvent such as water, a glycol or mixtures thereof, and toxicity adjustors, preservatives and buffers added as required. The resulting solution or dispersion is then sterilely filtered and used to fill sterile bottles.

The invention also provides a pharmaceutical composition comprising an antihypertensive effective amount of a compound of the formula (I) or pharmaceutically acceptable acid addition salts thereof together with a pharmaceutically acceptable diluent or carrier.

The compounds of the invention can be administered to humans for the treatment of hypertension or congestive heart failure by either the oral or parenteral routes, and may be administered orally at dosage levels approximately within the range 1 to 500 mg./day for an average adult patient (70 kg.), given in a single dose or up to 3 divided doses. Intravenous dosage levels would be expected to be about one-half to one-tenth of the daily oral dose. Thus for an average adult patient, individual oral doses in the tablet or capsule form will be approximately in the range from 0.5 to 250 mg. of the active compound. Variations will necessarily occur depending on the weight and condition of the subject being treated and the particular route of administration chosen as will be known to those skilled in the art.

The invention yet further provides a method of treating an animal, including a human being, having hypertension, which comprises administering to the animal an antihypertensive effective amount of a compound of the formula (I) or pharmaceutically acceptable acid addition salt thereof or pharmaceutical composition as defined above.

The following Examples illustrate the invention.

EXAMPLE 1

7,8-Dimethoxyquinazoline-2,4-dione (Xa)

Acetic acid (177.4 ml., 3.1 moles) was added to a vigorously stirred suspension of 3,4-dimethoxyanthranilic acid (436.5 g., 2.21 moles) in 10 liters of water. Then 2.24 liters of 20% potassium cyanate (5.53 moles) solution was gradually added and the mixture was stirred for one hour at 40° C. After cooling the reaction mixture to 20° C., 3.54 kg. sodium hydroxide pellets were added maintaining the temperature below 40° C. The reaction mixture was heated to 90° C. for 45 minutes and then slowly cooled in an ice bath. The sodium salt of the product was filtered, resuspended in 6 liters of water, acidified with concentrated hydrochloric acid (370 ml.), cooled and filtered to yield 404 grams (82%) of the product. Recrystallization from dimethylformamide gave colorless crystals, M.P. 314°–6° C.

Analysis, Percent Calcd. for $C_{10}H_{10}N_2O_4$: C, 54.05; H, 4.54; N, 12.61. Found: C, 53.96; H, 4.57; N, 12.63.

EXAMPLE 2

2,4-Dichloro-7,8-dimethoxyquinazoline (XIa)

A mixture of 7,8-dimethoxyquinazoline-2,4-dione (400 g., 1.80 moles), phosphorous pentachloride (750 g., 3.60 moles) and phosphorous oxychloride (4 liters was refluxed under nitrogen for three hours. Phosphorus oxychloride ($POCl_3$) was removed in vacuo and residual $POCl_3$ was removed as an azeotrope with toluene. The solid residue was slurried in eight liters of dichloromethane and the slurry slowly added to ice-cold $H_2O$. The suspension was stirred and unreacted starting material (54.0 g.) was filtered off. The organic layer was separated, dried over sodium sulfate and filtered. The solution was concentrated and then 4 liters of hexane was slowly added. Upon cooling, a pale yellow product (346 g., 80.4%) was collected by filtration and recrystallized from toluene/ether, M.P. 153°–5° C.

Analysis, Percent Calcd. for $C_{10}H_8Cl_2N_2O_2$: C, 46.35; H, 3.11; N, 10.81. Found: C, 46.14; H, 3.33; N, 10.60.

EXAMPLE 3

2-Chloro-4-amino-7,8-dimethoxyquinazoline (XIIa)

Ammonia was passed into a solution of 2,4-dichloro-7,8-dimethoxyquinazoline (287 g., 1.11 moles) in tetrahydrofuran (6 liters) for five hours at room temperature. After stirring an additional hour the suspension was concentrated in vacuo to 2 liters and filtered. The solid was suspended in 2 liters of water, filtered, washed with water and cold methanol. Recrystallization from dimethylformamide/water yielded 164 g. (62%) of pure product, M.P. 300°. (dec.).

Analysis, Percent Calcd. for $C_{10}H_{10}ClN_3O_2$: C, 50.11; H, 4.21; N, 17.53. Found: C, 50.07; H, 4.24; N, 17.58.

EXAMPLE 3A

When the appropriate starting material selected from those provided in Preparation I are employed in place of 3,4-dimethoxyanthranilic acid in the procedure of Example 1 and in each case the resulting product carried through the procedures of Examples 2 and 3, the following compounds are provided in a like manner.

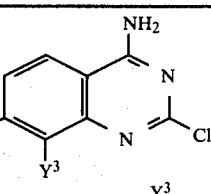

| $Y^2$ | $Y^3$ |
|---|---|
| $C_2H_5O$ | $C_2H_5O$ |
| $n$-$C_3H_7O$ | $n$-$C_3H_7O$ |
| $CH_3O$ | $C_2H_5O$ |
| $n$-$C_3H_7O$ | $CH_3O$ |
| $C_2H_5O$ | $CH_3O$ |
| $n$-$C_3H_7O$ | $C_2H_5O$ |

EXAMPLE 4

2-[4-(2-Furoyl)piperazine-1-yl]-4-amino-7,8-dimethoxyquinazoline hydrochloride A mixture of 2-chloro-4-amino-7,8-dimethoxyquinazoline (3.00 g., 12.5 mmoles) and 1-(2-furoyl)piperazine (2.71 g., 15.0 mmoles) was refluxed in 80 ml. isoamyl alcohol for two hours and then cooled in an ice-bath. The resulting white product was collected by filtration and recrystallized from methanol/ether to yield 4.53 g. (79%) of pure final product, M.P. 251° C. The water solubility was found to be 20 mg./ml.

Analysis, Percent Calcd. for $C_{19}H_{21}N_5O_4 \cdot HCl$: C, 54.34; H, 5.28; N, 16.68. Found: C, 54.14; H, 5.21; N, 16.42.

EXAMPLE 5

A. 6-Chloro-7,8-dimethoxyquinazoline-2,4-dione (Xb)

Acetic acid (10.5 g., 0.175 mole) was added to a vigorously stirred suspension of 5-chloro-3,4-dimethoxyanthranilic acid (28.9 g., 0.125 mole) in 600 ml. water. Then 506 ml. 5% potassium cyanate (0.312 mole) solution was gradually added and stirred 1 hour at 40° C. After cooling the reaction mixture to 20° C., 175 g. (4.37 moles) of sodium hydroxide pellets were added while maintaining the temperature below 40° C. The reaction mixture was heated to 90° C. for 45 minutes. Upon cooling in an ice bath, the sodium salt of the product precipitated, was filtered, resuspended in 125 ml. water, acidified with concentrated hydrochloric acid, cooled and filtered to yield 25.8 g. (80%) of colorless, pure product, M.P. 272°–3° C.

Analysis, Percent Calcd. for $C_{10}H_9ClN_2O_4$: C, 46.79; H, 3.53; N, 10.92. Found: C, 46.87; H, 3.60; N, 10.90.

B. 6-Chloro-7-methoxyquinazoline-2,4-dione (XVIII)

Similarly, 6-chloro-7-methoxyquinazoline-2,4-dione was prepared from 5-chloro-4-methoxyanthranilic acid in 83% yield, M.P. 356°–8° C.

Analysis, Percent Calcd. for $C_9H_7ClN_2O_3$: C, 47.70; H, 3.11; N, 12.36. Found: C, 47.72; H, 3.44; N, 12.27.

EXAMPLE 6

A. 2,4,6-Trichloro-7,8-dimethoxyquinazoline (XIb)

A mixture of 6-chloro-7,8-dimethoxyquinazoline-2,4-dione (25.5 g., 0.099 mole), phosphorous pentachloride (41.4 g., 0.199 mole) and 300 ml. phosphorous oxychloride was refluxed under nitrogen for three hours. Phosphorous oxychloride was removed in vacuo and residual $POCl_3$ was azeotroped with toluene. The reddish-orange solid was dissolved in 200 ml. dichloromethane and the solution was slowly added to ice-cold water. After stirring for 10 minutes the organic layer was separated, washed with water, and dried over sodium sulfate. The filtrate was concentrated and 150 ml. hexane was added slowly to precipitate the product as a pale yellow solid which was recrystallized from toluene/ether to afford 18.0 g. (62% yield), M.P. 154°–5° C.

Analysis, Percent Calcd. for $C_{10}H_7Cl_3N_2O_2$: C, 40.91; H, 2.40; N, 9.55. Found: C, 41.05; H, 2.48; N, 9.61.

B. 2,4,6-Trichloro-7-methoxyquinazoline (XIX)

Refluxing 6-chloro-7-methoxyquinazoline-2,4-dione with $PCl_5$ in $POCl_3$ as described above afforded 2,4,6-trichloro-7-methoxyquinazoline in 74% yield, M.P., 150°–2° C.

Analysis, Percent Cald. for $C_9H_5Cl_3N_2O$: C, 41.02; H, 1.91; N, 10.63. Found: C, 40.90; H, 2.01; N, 10.54.

EXAMPLE 7

A. 2,6-Dichloro-4-amino-7,8-dimethoxyquinazoline (XIIb)

Ammonia was passed into a solution of 2,4,6-trichloro-7,8-dimethoxyquinazoline (31.4 g., 0.107 mole) in 650 ml. dry tetrahydrofuran for one hour at room temperature. After stirring for an additional hour, the suspension was concentrated in vacuo and filtered. The solid was resuspended in water, filtered, washed with water and methanol. Recrystallization from dimethylformamide/water yielded 23.7 g. (81%) of the desired product, M.P., 360° C.

Analysis, Percent Calcd. for $C_{10}H_9Cl_2N_3O_2$: C, 43.82; H, 3.31; N, 15.33. Found: C, 43.95; H, 3.53; N, 15.35.

B. 2,6-Dichloro-4-amino-7-methoxyquinazoline (XX)

Reaction of 2,4,6-trichloro-7-methoxyquinazoline with ammonia as described above afforded 2,6-dichloro-4-amino-7-methoxyquinazoline as a white solid, M.P., 300° C. in 58% yield.

Analysis, Percent Calcd. for $C_9H_7Cl_2N_3O$: C, 44.28; H, 2.89; N, 17.22. Found: C, 44.12; H, 3.16; N, 17.19.

EXAMPLE 8

A. 2-[4-(2-Furoyl)piperazine-1-yl]-4-amino-6-chloro-7,8-dimethoxyquinazoline hydrochloride (XIIIb)

A mixture of 2,6-dichloro-4-amino-7,8-dimethoxyquinazoline (1.50 g., 5.47 mmole) and 1-(2-furoyl)piperazine (1.08 g., 5.99 mmole) was refluxed in 40 ml. isoamyl alcohol for 2 hours and then cooled overnight. The resulting solid was filtered and recrystallized from methanol/ether to yield 1.83 g. (74%) of pure final product, M.P., 208°–9° C.

Analysis, Percent Calcd. for $C_{19}H_{20}ClN_5O_4 \cdot HCl \cdot H_2O$: C, 49.25; H, 4.79; N, 15.17. Found: C, 49.03; H, 4.61; N, 15.35.

Water Solubility: 8 mg./ml.

B. 2-[4-(2-Furoyl)piperazine-1-yl]-4-amino-6-chloro-7-methoxyquinazoline hydrochloride The title compound was prepared similarly by refluxing 2,6-dichloro-4-amino-7-methoxyquinazoline and 1-(2-furoyl)piperazine in isoamyl alcohol, M.P. 229°–31° C., 79% yield.

Analysis, Percent Calcd. for $C_{18}H_{18}ClN_5O_3 \cdot HCl \cdot H_2O$: C, 48.88; H, 4.79; N, 15.83. Found: C, 49.47; H, 4.70; N, 15.62.

Water Solubility: 5 mg/ml.

EXAMPLE 9

A. 2-Methyl-2-hydroxypropyl 4-[4-amino-6-chloro-7,8-dimethoxyquinazolin-2-yl]piperazine-1-carboxylate hydrochloride A mixture of 2,6-dichloro-4-amino-7,8-dimethoxyquinazoline (1.50 g., 5.47 mmole) and 2-methyl-2-hydroxypropyl-4-piperazine-1-carboxylate (1.22 g., 6.03 mmole) was refluxed in 30 ml. methylisobutylketone for two days. The yellowish solid was filtered, resuspended in 40 ml. acetone and stirred for 15 minutes. The filtered solid was decolorized with charcoal and recrystallized twice from ethanol/ether to yield 1.47 g. (57%) of final product, M.P., 211°–3° C.

Analysis Percent Calcd. for $C_{19}H_{26}ClN_5O_5 \cdot HCl$; C, 47.90%; H, 5.50%; N, 14.70%. Found: C, 47.70%; H, 5.74; N, 14.36%.

Water Solubility: 35 mg./ml.

B. 2-ethyl-2-hydroxypropyl 4-[4-amino-6-chloro-7-methoxyquinazolin-2-yl]-piperazine-1-carboxylate hydrochloride [XXI, $R^1+R^2 = -COOCH_2C(OH)(CH_3)_2$]

The title compound was prepared similarly by refluxing 2,6-dichloro-4-amino-7-methoxy quinazoline and 2-methyl-2-hydroxypropyl-4-piperazine-1-carboxylate in methyl isobutyl ketone for 4 days, M.P. 243°–5° C., 69% yield.

Analysis Percent Calcd. for $C_{18}H_{24}ClN_5O_4 \cdot HCl \cdot H_2O$ C, 46.55%; H, 5.86%; N, 14.08%. Found: C, 46.89%; H, 5.67%; N, 15.22%.

Water Solubility: 6 mg./ml.

C. 2-[4-(1,4-Benzodioxan-2-carbonyl)piperazin-1-yl]-4-amino-6-chloro-7-methoxyquinazoline hydrochloride The title compound was prepared by the procedure of Part A, above, by refluxing 2,6-dichloro-4-amino-7-methoxyquinazoline and N-(1,4-benzodioxan-2-carbonyl)piperazine in methylisobutylketone, M.P. 194°–196° C.

EXAMPLE 10

When the appropriate N-substituted piperazine is employed in the procedure of Example 4 in place of 1-(2-furoyl)piperazine, the analogous products tabulated below are obtained as the hydrochloride salts except as otherwise noted.

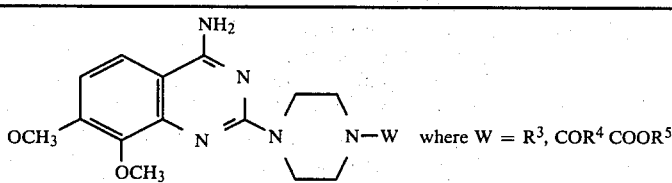

where W = R³, COR⁴ COOR⁵

| W | M.P. °C. | Solubility mg./ml. | Empirical Formula | Elemental Analysis Calcd.: Found: % C | % H | % N |
|---|---|---|---|---|---|---|
| COOR⁵: | | | | | | |
| COOCH₃ | 244–5 | 40 | $C_{16}H_{21}N_5O_4 \cdot HCl$ | 50.56 | 5.78 | 18.25 |
| | | | | 49.69 | 5.74 | 18.24 |
| COOCH₂CH₃ | 238–40 | 50 | $C_{17}H_{23}N_5O_4 \cdot HCl$ $\cdot 0.25 H_2O$ | 50.74 | 6.13 | 17.41 |
| | | | | 50.83 | 6.03 | 17.25 |
| COO(CH₂)₂CH₃ | 229–30 | 140 | $C_{18}H_{25}N_5O_4 \cdot HCl$ | 52.48 | 6.36 | 17.00 |
| | | | | 52.28 | 6.37 | 16.82 |
| COO(CH₂)₃CH₃ | 224–6 | 90 | $C_{19}H_{27}N_5O_4 \cdot HCl$ | 53.58 | 6.63 | 16.44 |
| | | | | 53.28 | 6.34 | 16.22 |
| COO(CH₂)₄CH₃ | 114–6 | 40 | $C_{20}H_{29}N_5O_4 \cdot HCl$ | 54.60 | 6.87 | 15.92 |
| | | | | 54.73 | 6.98 | 15.92 |
| COOCH₂CH(CH₃)₂ | 212–3.5 | 40 | $C_{19}H_{27}N_5O_4 \cdot HCl$ | 53.58 | 6.63 | 16.44 |
| | | | | 53.82 | 6.70 | 15.79 |
| COOR⁵: | | | | | | |
| COO(CH₂)₂CH(CH₃)₂ | 192 | 25 | $C_{20}H_{29}N_5O_4 \cdot HCl$ | 54.60 | 6.87 | 15.92 |
| | | | | 54.99 | 7.18 | 15.91 |
| COOCH₂C(CH₃)₂OH | 165–70 | — | $C_{19}H_{27}N_5O_4 \cdot HCl$ $\cdot 0.5 H_2O$ | 48.66 | 6.66 | 14.93 |
| | | | | 48.81 | 6.59 | 14.83 |
| COR⁴: —C(=O)-tetrahydrofuryl | 237–8 | 150 | $C_{19}H_{25}N_5O_4 \cdot HCl$ $\cdot 0.5 H_2O$ | 52.71 | 6.29 | 16.18 |
| | | | | 53.03 | 5.95 | 16.16 |
| —C(=O)-thienyl | 237–8.5 | 11 | — | — | — | — |
| —C(=O)CH(CH₃)₂ | — | — | — | — | — | — |
| —C(=O)—H | 251–3 | — | $C_{15}H_{19}N_5O_3 \cdot HCl$ $\cdot H_2O$ | 48.45 | 5.96 | 18.83 |
| | | | | 48.30 | 5.65 | 18.72 |
| —C(=O)—C₆H₅ | 192–201 | 50 | $C_{21}H_{23}N_5O_3 \cdot HCl$ $\cdot 0.5 H_2O$ | 57.46 | 5.74 | 15.96 |
| | | | | 56.99 | 5.66 | 15.87 |
| —C(=O)-pyrrolidinyl | — | — | $C_{19}H_{26}N_6O_3$ | — | — | — |
| —C(=O)-benzodioxinyl | 150 (dec) | 15 | $C_{23}H_{25}N_5O_5 \cdot HCl$ $\cdot H_2O$ | 54.59 | 5.58 | 13.84 |
| | | | | 54.27 | 5.39 | 13.85 |
| —C(=O)—CH₂CH₃ | — | — | — | — | — | — |
| —C(=O)-cyclopentyl | 158–61 | — | $C_{20}H_{27}N_5O_3$ (free base) | 62.32 | 7.06 | 18.17 |
| | | | | 62.10 | 7.27 | 18.19 |
| R³: CH₂CH₂OH | 205–8 | 95 | $C_{16}H_{23}N_5O_3 \cdot HCl$ | 48.71 | 6.54 | 18.94 |
| | | | | 50.01 | 6.55 | 18.85 |
| CH₂C₆H₅ | 194–8 (dec) | 100 | $C_{21}H_{25}N_5O_2 \cdot HCl$ $\cdot 2 H_2O$ | 55.80 | 6.69 | 15.49 |
| | | | | 55.38 | 6.49 | 15.33 |
| C₆H₅ | 185–7 | 25 | $C_{20}H_{23}N_5O_2 \cdot HCl$ | 59.77 | 6.02 | 17.43 |
| | | | | 59.10 | 6.09 | 17.23 |
| 3-CF₃C₆H₄— | 218–9 | 8 | $C_{21}H_{22}N_5O_2F_3 \cdot HCl$ | 53.67 | 4.93 | 14.90 |
| | | | | 53.97 | 4.88 | 15.12 |
| —CH₂CH=CH₂ | 195–6 | 50 | $C_{17}H_{23}N_5O_2 \cdot HCl$ $\cdot 0.5 H_2O$ | 54.46 | 6.72 | 18.68 |
| | | | | 53.73 | 6.46 | 18.44 |

EXAMPLE 11

2-[4-(2-Furoyl-homopiperazine-1-yl]-4-amino-7,8-dimethoxyquinazoline hydrochloride

A. N-(2-Furoyl)homopiperazine

Homopiperazine (70 g., 0.70 mole) in 160 ml. water was treated with 6 N hydrochloric acid to adjust to pH 5.5 Furoyl chloride (79.5 g., 0.60 mole) and 25% (w/w) aqueous sodium hydroxide solution were added simultaneously to maintain a pH of 4.5–5.5. Then additional sodium hydroxide was added to bring the mixture to pH 9.5. The solution was extracted with chloroform, dried over anhydrous potassium carbonate and distilled to afford 63 g. of product, B.P. 124°–130° C. at 10 mm.

B. 4-Amino-2-dimethoxyquinazoline (1.76 g., 7.3 mole), N-(2-furoyl)homopiperazine (1.50 g., 7.7 mole) and 40 ml. of isoamyl alcohol were combined and the mixture heated at reflux under a nitrogen atmosphere for 1.5 hours. After cooling to room temperature, the mixture was stirred for one hour, filtered and the precipitated product washed with ether and recrystallized from methanol/ether to afford 2.15 g. of the title compound, M.P. 182°–183° C.

Analysis, Percent Calcd. for $C_{20}H_{23}N_5O_4 \cdot HCl \cdot 0.5-H_2O$: C, 54.23; H, 5.69; N, 15.81. Found: C, 53.84; H, 5.40; N, 15.49.

The solubility in water was found to be 30 mg./ml.

EXAMPLE 12

2-[4-(2-Tetrahydrofuroyl)homopiperazin-1-yl]-4-amino7,8-dimethoxyquinazoline hydrochloride

A. N-(2-Tetrahydrofuroyl)homopiperazine

N-[2-Furoyl]homopiperazine (33.0 g.) in 200 ml. of ethanol was hydrogenated over 5% rhodium-on-carbon catalyst at three atmospheres pressure. The catalyst was removed by filtration and the product distilled to give the desired product, B.P. 135° at 1 mm.

B. 4-Amino-2-chloro-7,8-dimethoxyquinazoline (2.10 g., 8.75 mmole), N-(2-tetrahydrofuroyl)homopiperazine (1.9 g., 9.58 mmole) and 50 ml. of isoamyl alcohol were mixed and heated at reflux under nitrogen for 2.5 hours. The solvent was removed by evaporation in vacuo, the residue dissolved in water and filtered through a mixture of activated carbon and diatomaceous earth. The filtrate was adjusted to an alkaline pH by addition of sodium bicarbonate solution, extracted four times with 50 ml. portions of ethyl acetate and the extracts dried over sodium sulfate. The solvent was evaporated and the residue chromatographed on 30 g. of silica gel, eluting with chloroform/ethanol. The fractions containing the desired product (free base) were combined and evaporated to afford the free base as a foam, 1.0 g. The free base was dissolved in ether, saturated hydrogen chloride and filtered to obtain the title compound, M.P. 130° (dec.).

Analysis, Percent Calcd. for $C_{20}H_{27}N_5O_4 \cdot HCl \cdot 0.50-H_2O$: C, 53.74; H, 6.54; N, 15.67. Found: C, 53.56; H, 6.68; N, 15.44.

Water Solubility: 120 mg./ml.

EXAMPLE 13

A.

2-(4-Benzylpiperidin-1-yl)-4-amino-7,8-dimethoxyquinazoline hydrochloride

4-Amino-2-chloro-7,8-dimethoxyquinazoline (2.40 g., 10 mmole), 4-benzylpiperidine (1.93 g., 11 mmole) and 50 ml. of isoamyl alcohol were heated at reflux under a nitrogen atmosphere for two hours and cooled to room temperature. Diethyl ether (50 ml.) was added and the mixture allowed to stand in the refrigerator for two days. The precipitated solid was collected by filtration and recrystallized from ethanol/diethyl ether to afford 2.50 g. (60%) of the title compound, M.P. 216°–217° C.

Analysis, Percent Calc'd. for $C_{22}H_{26}O_2N_4 \cdot HCl$ C, 63.68; H, 6.56; N, 13.50 Found: C, 63.78; H, 6.67; N, 13.89.

Water Solubility: 6 mg./ml.

EXAMPLE 14

Employing the appropriately substituted 2-chloro-(or 2-bromo) 4-amino quinazoline and amine of formula

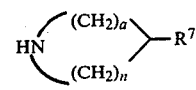

in the procedure of Example 13 the following products are obtained.

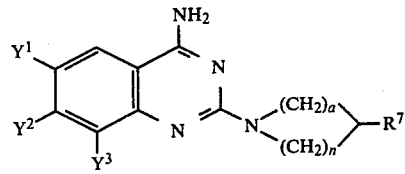

where a is 1 or m and m and n are 2, or 3.

| $Y^1$ | $Y^2$ | $Y^3$ | a | n | $R^7$ |
|---|---|---|---|---|---|
| H | $CH_3O$ | $CH_3O$ | 1 | 2 | $CH_3$ |
| Cl | $CH_3O$ | H | 1 | 2 | $CH_3(CH_2)_5$ |
| Cl | $CH_3O$ | $CH_3O$ | 1 | 2 | $(CH_3)_2CHCH_2$ |
| H | $C_2H_5O$ | $C_2H_5O$ | 1 | 2 | $C_6H_5$ |
| Cl | $C_2H_5O$ | H | 1 | 2 | $C_6H_5CH_2$ |
| Cl | $C_2H_5O$ | $C_2H_5O$ | 1 | 2 | $3\text{-}CH_3C_6H_4$ |
| H | $nC_3H_7O$ | $CH_3O$ | 1 | 3 | $(CH_3)_2CH$ |
| Cl | $nC_3H_7O$ | H | 1 | 3 | $CH_3(CH_2)_4$ |
| Cl | $nC_3H_7O$ | $n\text{-}C_3H_7O$ | 1 | 3 | $3\text{-}FC_6H_4$ |
| H | $CH_3O$ | H | 1 | 3 | $4\text{-}CH_3OC_6H_4CH_2$ |
| Cl | $CH_3O$ | $CH_3O$ | 2 | 2 | $4\text{-}HOC_6H_4$ |
| Cl | $CH_3O$ | $CH_3O$ | 2 | 2 | $3\text{-}CH_3SO_2C_6H_4$ |
| H | $CH_3O$ | $CH_3O$ | 2 | 2 | $2\text{-}CH_3SO_2NHC_6H_4CH_2$ |
| Cl | $CH_3O$ | H | 2 | 3 | $CH_3CH_2$ |
| Cl | $CH_3O$ | $CH_3O$ | 2 | 3 | $4\text{-}CH_3SO_2NHC_6H_4$ |
| H | $C_2H_5O$ | H | 2 | 3 | $CH_3(CH_2)_3$ |
| Cl | $CH_3O$ | $CH_3O$ | 2 | 3 | $4\text{-}CF_3C_6H_4CH_2$ |
| Cl | $CH_3O$ | $CH_3O$ | 2 | 3 | $4\text{-}FC_6H_4$ |
| H | $CH_3O$ | $n\text{-}C_3H_7O$ | 3 | 3 | $CH_3$ |
| Cl | $n\text{-}C_3H_7O$ | H | 3 | 3 | $C_6H_5$ |
| Cl | $CH_3O$ | H | 3 | 3 | $C_6H_5CH_2$ |
| H | $CH_3O$ | $CH_3O$ | 3 | 3 | $4\text{-}CH_3C_6H_4$ |
| Cl | $CH_3O$ | $CH_3O$ | 1 | 3 | $2\text{-}ClC_6H_4CO$ |
| Cl | $CH_3O$ | H | 1 | 3 | $C_6H_5CO$ |
| H | $CH_3O$ | $CH_3O$ | 1 | 2 | $4\text{-}BrC_6H_4CO$ |
| Cl | $CH_3O$ | H | 1 | 2 | $4\text{-}HOC_6H_4CO$ |
| Cl | $CH_3O$ | $CH_3O$ | 2 | 2 | $4\text{-}CF_3C_6H_4CO$ |
| H | $CH_3O$ | $CH_3O$ | 2 | 3 | $4\text{-}FC_6H_4CO$ |
| Cl | $CH_3O$ | H | 3 | 3 | $3\text{-}CH_3SO_2C_6H_4CO$ |
| Cl | $CH_3O$ | H | 1 | 3 | $C_6H_5CO$ |
| H | $CH_3O$ | $CH_3O$ | 1 | 2 | $HOCH_2$ |
| Cl | $CH_3O$ | $CH_3O$ | 1 | 2 | $HOCH_2CH_2$ |
| Cl | $CH_3O$ | H | 1 | 2 | $(CH_3)_2C(OH)CH_2$ |
| H | $CH_3O$ | $CH_3O$ | 1 | 3 | $(CH_3)_2CHCH(OH)CH_2$ |
| Cl | $CH_3O$ | $CH_3O$ | 1 | 3 | $(CH_3)_2C(OH)CH_2CH_2$ |
| Cl | $CH_3O$ | H | 1 | 3 | $(CH_3)_2C(OH)$ |
| H | $CH_3O$ | $CH_3O$ | 2 | 2 | $CH_2OH$ |
| Cl | $CH_3O$ | $CH_3O$ | 2 | 2 | $CH_2CH_2OH$ |
| Cl | $CH_3O$ | H | 2 | 2 | $CH_3CH(OH)$ |
| H | $C_2H_5O$ | $C_2H_5O$ | 3 | 3 | $CH_2OH$ |
| Cl | $CH_3O$ | $CH_3O$ | 3 | 3 | $(CH_3)_2C(OH)$ |

| Y¹ | Y² | Y³ | a | n | R⁷ |
|---|---|---|---|---|---|
| Cl | CH₃ | H | 3 | 3 | (CH₃CH₂)₂C(OH) |

EXAMPLE 15

2-[4-(2-Tetrahydrofuroyl)piperazin-1-yl]-4-amino-6-chloro-7,8-dimethoxyquinazoline To 35 ml. of isoamyl alcohol were added 1.50 g. (5.47 mmole) of 4-amino-2,6-dichloro-7,8-dimethoxyquinazoline and 1.11 g. (6.02 mmole) of 1-(2-tetrahydrofuroyl)-piperazine and the mixture was heated at reflux under a nitrogen atmosphere for 1.5 hours. The mixture was cooled, 20 ml. of ethyl ether was added and the resulting mixture stirred at room temperature overnight. It was then cooled in ice and the precipitated solid collected by filtration. The crude material was recrystallized once from a mixture of isopropanol, methanol and ethyl ether. The recrystallized material was dissolved in water made strongly alkaline with sodium hydroxide solution while stirring, the precipitated brownish solid collected by filtration, dried, decolorized with activated carbon and recrystallized from isopropanol/ethyl ether to obtain 0.38 g. of yellow solid, M.P. 192°–193° C.

Analysis, Percent Calc'd. for $C_{19}H_{24}O_4N_5Cl$: C, 54.09; H, 5.73; N, 16.60 Found: C, 53.83; H, 5.73; N, 16.58.

Mass spectrum peaks (M+/e); 421 (molecular ion), 406, 392, 378, 350, 321, 293, 280 and 266.

EXAMPLE 16

Employing the procedures of Examples 8, 9 and 10 the following compounds are similarly prepared from the appropriate starting materials.

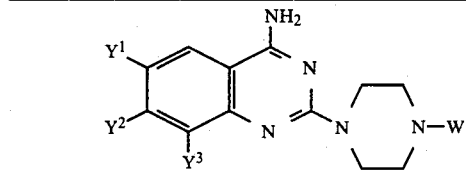

| Y¹ | Y² | Y³ | W |
|---|---|---|---|
| H | CH₃O | CH₃O | H |
| Cl | C₂H₅O | C₂H₅O | CH₃ |
| H | n-C₃H₇O | n-C₃H₇O | CH₂CH(CH₃)₂ |
| Cl | iso-C₃H₇O | H | CH₂(CH₂)₄CH₃ |
| H | CH₃O | CH₃O | CH₂CH=CH₂ |
| Cl | CH₃O | CH₃O | CH₂C(CH₃)=CH₂ |
| H | C₂H₅O | C₂H₅O | CH₂CH=CHCH₃ |
| Cl | C₂H₅O | H | CH₂C(CH₃)=CHCH₃ |
| H | n-C₃H₇O | n-C₃H₇O | CH₂(CH₂)₂CH=CH₂ |
| Cl | n-C₃H₇O | n-C₃H₇O | CH₂CH₂OH |
| H | iso-C₃H₇O | CH₃O | CH₂CH₂OH |
| Cl | CH₃O | H | CH₂CH(OH)CH₃ |
| H | CH₃O | CH₃O | CH₂C(OH)(CH₃)₂ |
| Cl | CH₃O | CH₃O | CH(CH₃)CH(CH₃)CH₂OH |
| H | C₂H₅O | C₂H₅O | CH₂C(CH₃)₂CH₂OH |
| Cl | C₂H₅O | H | C(CH₃)₂C(OH)CH₃ |
| H | C₂H₅O | C₂H₅O | cyclopropyl |
| Cl | n-C₃H₇O | n-C₃H₇O | cyclopentyl |
| H | n-C₃H₇O | n-C₃H₇O | cyclohexyl |
| Cl | CH₃O | H | cyclooctyl |
| H | CH₃O | CH₃O | 4-ClC₆H₄ |
| Cl | CH₃O | H | 2-FC₆H₄ |
| H | CH₃O | CH₃O | 4-CH₃OC₆H₄CH₂ |
| Cl | CH₃O | H | 3-CF₃C₆H₄CH₂ |
| H | CH₃O | CH₃O | 4-HOC₆H₄ |
| H | CH₃O | CH₃O | 2-CH₃SO₂C₆H₄ |
| Cl | CH₃O | CH₃O | 4-CH₃SO₂NHC₆H₄ |

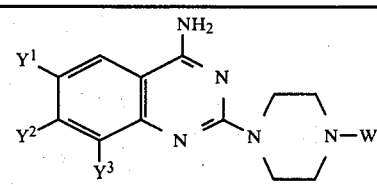

| Y¹ | Y² | Y³ | W |
|---|---|---|---|
| Cl | C₂H₅O | H | 4-CH₃SO₂NHC₆H₄CH₂ |
| Cl | C₂H₅O | C₂H₅O | 4-CH₃SO₂C₆H₄CH₂ |
| Cl | C₂H₅O | H | 4-BrC₆H₄CH₂ |
| Cl | C₂H₅O | C₂H₅O | 2-CH₃C₆H₄CH₂ |
| Cl | C₂H₅O | H | 3-FC₆H₄CH₂ |
| Cl | CH₃O | H | 2-fluoro-1-naphthyl |
| H | CH₃O | CH₃O | 4-bromo-2-naphthyl |
| H | CH₃O | CH₃O | 4-methyl-1-naphthyl |
| H | CH₃O | CH₃O | 3-trifluoromethyl-1-naphthyl |
| Cl | CH₃O | CH₃O | 2-hydroxy-1-naphthyl |
| H | CH₃O | CH₃O | 4-hydroxy-1-naphthylmethyl |
| Cl | CH₃O | H | 4-methoxy-2-naphthylmethyl |
| Cl | CH₃O | CH₃O | 3-fluoro-1-naphthylmethyl |
| H | CH₃O | CH₃O | 6-methylsulfonylamino-1-naphthylmethyl |
| H | CH₃O | CH₃O | 4-methylsulfonyl-1-naphthyl |
| H | CH₃O | CH₃O | CH₂C≡CH |
| Cl | CH₃O | CH₃O | CH₂C≡CCH₃ |
| Cl | CH₃O | CH₃O | CH₂C=CCH₂CH₃ |
| H | CH₃O | CH₃O | CH₂(CH₂)₂C≡CH |
| Cl | CH₃O | H | CHO |
| Cl | CH₃O | H | COCH₃ |
| H | iso-C₃H₇O | iso-C₃H₇O | COCH(CH₃)₂ |
| H | C₂H₅O | C₂H₅O | CO—CH₂(CH₂)₄CH₃ |
| Cl | CH₃O | CH₃O | COCH₂(CH₂)₂CH(CH₃)₂ |
| Cl | CH₃O | H | COCH₂CH=CH₂ |
| H | n-C₃H₇O | n-C₃H₇O | COCH₂C(CH₃)=CH₂ |
| Cl | CH₃O | CH₃O | COCH₂C(CH₃)=CHCH₃ |
| Cl | CH₃O | H | COCH₂C≡CH |
| H | CH₃O | CH₃O | COCH₂C≡CCH₃ |
| H | CH₃O | CH₃O | COC≡CCH₂CH₂CH₃ |
| Cl | CH₃O | CH₃O | cyclopropylcarbonyl |
| H | CH₃O | CH₃O | cyclobutylcarbonyl |
| H | C₂H₅O | C₂H₅O | cycloheptylcarbonyl |
| H | CH₃O | CH₃O | cyclooctylcarbonyl |
| H | CH₃O | CH₃O | cyclopropylmethylcarbonyl |
| Cl | CH₃O | H | cyclooctylmethylcarbonyl |
| Cl | CH₃O | H | 3-thenoyl |
| H | CH₃O | CH₃O | 5-chloro-2-thenoyl |
| H | CH₃O | CH₃O | 4-methyl-3-thenoyl |
| Cl | CH₃O | CH₃O | 5-phenyl-2-thenoyl |
| H | CH₃O | CH₃O | 5-ethyl-3-furoyl |
| H | CH₃O | CH₃O | 5-phenyl-2-furoyl |
| H | CH₃O | CH₃O | 2-pyridylcarbonyl |
| H | CH₃O | CH₃O | 2-chloro-4-pyridylcarbonyl |
| Cl | CH₃O | H | 2-methyl-4-pyrimidinylcarbonyl |
| H | CH₃O | CH₃O | 2-phenyl-4-pyrimidinylcarbonyl |
| H | CH₃O | CH₃O | ![tetrahydrofuroyl] |
| Cl | CH₃O | CH₃O | ![tetrahydrothiofuroyl] |
| Cl | CH₃O | H | ![thienyl-CO] |
| H | CH₃O | CH₃O | ![dioxanylcarbonyl] |
| H | CH₃O | CH₃O | ![chromanylcarbonyl] |
| Cl | CH₃O | H | ![benzofuranylcarbonyl] |

-continued

Structure: 4-amino-quinazoline with Y¹, Y², Y³ substituents on benzene ring and 2-piperazinyl group with N-W substituent.

| Y¹ | Y² | Y³ | W |
|---|---|---|---|
| Cl | CH₃O | CH₃O | (2,3-dihydrobenzothiopyran-2-yl)-CH₂CO |
| Cl | CH₃O | CH₃O | (1,4-benzodioxan-2-yl)-CH₂CO |
| H | CH₃O | CH₃O | (1,4-dioxan-2-yl)-CH₂CO |
| H | CH₃O | CH₃O | (tetrahydrofuran-2-yl)-CH₂CO |
| Cl | CH₃O | H | (tetrahydrothiopyran-2-yl)-CH₂CO |
| Cl | CH₃O | H | 1-hydroxy-2-naphthoyl |
| H | CH₃O | CH₃O | 4-chloro-1-naphthylmethyl-carbonyl |
| Cl | CH₃O | H | (5-methyl-tetrahydrofuran-2-yl)-CO |
| Cl | CH₃O | CH₃O | (thiazol-5-yl)-CO |
| H | CH₃O | CH₃O | (2-methylthio-thiazol-5-yl)-CO |
| H | CH₃O | CH₃O | (oxazol-5-yl)-CO |
| Cl | CH₃O | H | (2-methylthio-oxazol-5-yl)-CO |
| H | CH₃O | CH₃O | (5-methylthio-1,3,4-oxadiazol-2-yl)-CO |
| Cl | CH₃O | CH₃O | (5-methylthio-1,3,4-thiadiazol-2-yl)-CO |
| Cl | CH₃O | H | (pyrrolidin-2-yl)-CO |
| H | CH₃O | CH₃O | (2-n-C₄H₉-1,3,4-thiadiazol-5-yl)-CO |
| Cl | CH₃O | H | (2-NHCOOC₂H₅-1,3,4-thiadiazol-5-yl)-CO |
| H | CH₃O | CH₃O | (2-n-C₄H₉-1,3,4-thiadiazol-5-yl)-CO (with n-C₄H₉ label) |
| Cl | CH₃O | H | CH₃OCO |
| H | CH₃O | CH₃O | CH₃(CH₂)₅CH₂OCO |
| Cl | CH₃O | CH₃O | cyclohexyl OCO |
| H | CH₃O | CH₃O | HOCH₂CH₂OCO |
| Cl | CH₃O | H | (CH₃)₂C(OH)CH₂CH₂OCO |
| Cl | CH₃O | CH₃O | 4-BrC₆H₄CH₂OCO |
| H | CH₃O | CH₃O | 1-hydroxy-2-naphthylmethyl-OCO |
| H | CH₃O | CH₃O | CH₂=CH—CH₂OCO |
| Cl | CH₃O | CH₃O | CH₂=C(CH₃)CH₂OCO |
| Cl | CH₃O | H | CH₃CH=C(CH₃)CH₂OCO |
| Cl | C₂H₅O | H | cyclopropyl-OCO |
| Cl | n-C₃H₇O | H | cyclohexyl-OCO |
| H | n-C₃H₇O | n-C₃H₇O | cycloheptyl-OCO |
| Cl | CH₃O | CH₃O | cyclooctyl-OCO |
| Cl | C₂H₅O | C₂H₅O | CH₃CH(OH)CH₂OCO |
| H | C₂H₅O | C₂H₅O | 2-CH₃C₆H₄CH₂OCO |
| Cl | CH₃O | CH₃O | 3-CF₃C₆H₄CH₂OCO |
| Cl | CH₃O | CH₃O | 4-CH₃OC₆H₄CH₂OCO |
| Cl | CH₃O | H | 4-HOC₆H₄CH₂OCO |
| Cl | CH₃O | H | 3-CH₃SO₂C₆H₄CH₂OCO |
| H | CH₃O | CH₃O | 4-CH₃SO₂NHC₆H₄CH₂OCO |
| H | CH₃O | CH₃O | 4-chloro-1-naphthylmethyl-OCO |
| Cl | CH₃O | H | 1-fluoro-2-naphthylmethyl-OCO |
| Cl | CH₃O | CH₃O | 3-hydroxy-2-naphthylmethyl-OCO |
| Cl | CH₃O | CH₃O | 2-methyl-1-naphthylmethyl-OCO |
| H | CH₃O | CH₃O | 1-methoxy-2-naphthylmethyl-OCO |
| Cl | CH₃O | H | 4-trifluoromethyl-1-naphthyl-methyl-OCO |
| Cl | CH₃O | H | (3-SO₂CH₃-naphth-2-yl)-CH₂OCO |
| Cl | CH₃O | CH₃O | (3-NHSO₂CH₃-naphth-2-yl)-CH₂OCO |
| H | CH₃O | CH₃O | (pyridin-3-yl)-OCH₂OCO |
| Cl | CH₃O | CH₃O | (pyridin-4-yl)-OCH₂OCO |
| H | CH₃O | CH₃O | (tetrahydrothiophen-2-yl)-CH₂OCO |
| Cl | CH₃O | CH₃O | (tetrahydrofuran-2-yl)-CH₂OCO |
| Cl | CH₃O | H | (1,4-dioxan-2-yl)-CH₂OCO |
| Cl | CH₃O | H | (tetrahydropyran-2-yl)-CH₂OCO |
| H | C₂H₅O | C₂H₅O | (tetrahydrothiopyran-2-yl)-CH₂OCO |
| Cl | CH₃O | H | (1,4-benzodioxan-2-yl)-CH₂OCO |

-continued $$\text{structure with } Y^1, Y^2, Y^3 \text{ substituents, } NH_2 \text{ group, and piperazine ring with N-W}$$

| $Y^1$ | $Y^2$ | $Y^3$ | W |
|---|---|---|---|
| Cl | $C_2H_5O$ | H | benzofuran-CH$_2$OCO |
| Cl | $CH_3O$ | $CH_3O$ | benzothiophene-CH$_2$OCO |
| H | $CH_3O$ | $CH_3O$ | benzofuran-CO |
| Cl | $CH_3O$ | $CH_3O$ | benzofuran-CO |
| Cl | $CH_3O$ | H | benzothiophene-CO |
| H | $CH_3O$ | $CH_3O$ | benzofuran-CH$_2$CO |
| Cl | $CH_3O$ | $CH_3O$ | benzothiophene-CH$_2$CO |
| Cl | $CH_3O$ | H | benzothiophene-CH$_2$OCO |
| H | $CH_3O$ | $CH_3O$ | benzofuran-CH$_2$OCO |

EXAMPLE 17

A. 3-Chloro-4-methoxy-6-isothiocyanatobenzonitrile

To a solution of 27.4 g. (0.15 mole) of 6-amino-3-chloro-4-methoxybenzonitrile in 150 ml. of 1,2-dichloro-ethane at 0°–5° C. is added with stirring a mixture of 23 g. (0.2 mole) thiophosgene, 100 ml. 1,2-dichloroethane, 20 g. (0.2 mole) calcium carbonate and 200 ml. of water. After the addition the mixture is stirred for one hour at 0°–5° C., warmed to 20° C. and stirred for 6 hours at this temperature and finally at 35° C. for an hour. The reaction mixture is filtered and the organic layer separated, washed with dilute hydrochloric acid, water and dried (MgSO$_4$). The solvent is removed by evaporation and the residue used without purification in the next step.

B. 3-Chloro-4-methoxy-6-(homomorpholin-4-yl)thiocarbamidobenzonitrile

To 11.3 g. (0.05 mole) of the above residue dissolved in 65 ml. of ethyl acetate is slowly added with stirring at 0° C., a solution of 5.1 g. (0.05 mole) of homomorpholine in an equal volume of the same solvent. The resulting mixture is cooled to −25° C. and allowed to stand overnight. The precipitate is collected by filtration, washed with cold ethyl acetate and dried to obtain the desired product.

C. N-(3-Methoxy-4-chloro-6-cyanophenyl)-(homomorpholin-4-yl)-methylthioformamidate In 200 ml. of diglyme (diethylene glycol dimethylether) is dissolved 16.3 g. (0.05 mole) of 3-chloro-4-methoxy-6-(homomorpholin-4-yl)-thiocarbamidobenzonitrile and 14.2 g. (0.1 mole) of methyl iodide and the mixture heated at reflux (60° C.) for eight hours then cooled to room temperature. The resulting mixture is filtered, the solid product washed with ether and dried to obtain the hydroiodide salt of the title compound.

The hydroiodide salt is dissolved in 150 ml. of methanol and 90 ml. of 25% ammonium hydroxide is added with stirring. The resulting mixture is stirred for two hours at 0° C., filtered and washed with ether to obtain the title compound as the free base.

D. 2-(Homomorpholin-4-yl)-4-amino-6-chloro-7-methoxyquinazoline

To a solution of 3.4 g. (0.01 mole) of the free base obtained in Part C, above, in 75 ml. of formamide is added 1.3 g. of sodium amide and the resulting solution is cooled to 0° C. and saturated with ammonia gas. The cold solution is warmed slowly over 2–3 hours to 120° C., then maintained at this temperature for 4 hours. The reaction mixture is then cooled to room temperature, 100 ml. of ice-water added, the mixture extracted with chloroform, the extracts washed with water, dried and evaporated to dryness. The crude residual product is purified by crystallization.

EXAMPLE 18

Employing one of the procedures of Examples 4, 8, 9 and 17, the following compounds are prepared from the appropriate starting materials.

| $Y^1$ | $Y^2$ | $Y^3$ | $R^1$ | $R^2$ |
|---|---|---|---|---|
| H | $CH_3O$ | $CH_3O$ | H | H |
| H | $CH_3O$ | $CH_3O$ | H | $CH_3$ |
| Cl | $CH_3O$ | $CH_3O$ | H | $(CH_3)_2CH$ |
| Cl | $CH_3O$ | H | H | $(CH_3)_2CHCH(CH_3)$ |
| Cl | $C_2H_5O$ | H | $CH_3$ | $CH_3$ |
| H | $CH_3O$ | $CH_3O$ | $CH_3(CH_2)_3CH_2$ | $CH_3CH_2$ |
| Cl | $CH_3O$ | $CH_3O$ | $CH_3(CH_2)_3CH_2$ | $CH_3(CH_2)_3CH_2$ |

-continued

[Structure: benzene ring with NH₂ group at top, Y¹, Y², Y³ substituents, and N=C(NR¹R²)-N fused ring system (quinazoline-like)]

| Y¹ | Y² | Y³ | R¹ | R² |
|---|---|---|---|---|
| Cl | CH₃O | CH₃O | H | cyclopropyl |
| Cl | CH₃O | H | CH₃ | cyclopentyl |
| H | CH₃O | CH₃O | H | cyclooctyl |
| H | CH₃O | CH₃O | cyclopropyl | cyclopropyl |
| Cl | CH₃O | CH₃O | cyclohexyl | cyclohexyl |
| Cl | CH₃O | H | cyclohexyl | cyclooctyl |
| Cl | CH₃O | H | CH₂=CH—CH₂ | CH₂=CHCH₂ |
| H | n-C₃H₇O | n-C₃H₇O | CH₂=CH(CH₂)₃ | CH₂=CH(CH₂)₃ |
| Cl | CH₃O | H | CH₂=C(CH₃)CH₂ | CH₂=C(CH₃)CH₂ |
| Cl | CH₃O | CH₃O | CH₃ | CH₂=CHCH₂ |
| Cl | CH₃O | CH₃O | H | CH₂=CHCH₂ |
| H | CH₃O | CH₃O | H | (CH₃)₂C=CHCH₂ |
| H | CH₃O | CH₃O | H | CH≡CCH₂ |
| Cl | CH₃O | CH₃O | H | CH≡C(CH₂)₃ |
| Cl | CH₃O | H | CH₃CH₂CH₂ | CH≡CCH₂ |
| Cl | CH₃O | CH₃O | cyclopropyl | CH₃C≡CCH₂ |
| Cl | CH₃O | CH₃O | cyclohexyl | CH≡CCH₂ |
| H | CH₃O | CH₃O | CH₂=CHCH₂ | CH≡CCH₂ |
| H | CH₃O | CH₃O | CH₃(CH₂)₄CH₂ | CH₂=CHCH₂ |
| H | CH₃O | CH₃O | cyclooctyl | CH₃CH=CHCH₂ |
| Cl | CH₃O | H | CH₃(CH₂)₃CH₂ | (CH₃)₂C=CHCH₂ |
| Cl | CH₃O | H | HOCH₂CH₂ | HOCH₂CH₂ |
| H | CH₃O | CH₃O | H | HO(CH₂)₅ |
| Cl | CH₃O | CH₃O | H | HOCH₂CH₂ |
| Cl | CH₃O | H | HO(CH₂)₅ | HO(CH₂)₅ |
| Cl | CH₃O | H | CH₃ | HOCH₂CH₂CH₂ |
| H | CH₃O | CH₃O | (CH₃)₂CHCH₂CH₂ | HOCH₂CH₂ |
| Cl | CH₃O | CH₃O | cyclohexyl | CH₃CH(OH)CH₂ |
| Cl | CH₃O | H | CH₂=CHCH₂ | (CH₃)₂C(OH)CH₂ |
| H | CH₃O | CH₃O | CH≡CCH₂ | HO(CH₂)₅ |
| H | CH₃O | CH₃O | cyclopropyl | HOCH₂CH₂ |

EXAMPLE 19

A.
2-(3-Thiazolidinyl)-4-amino-7,8-dimethoxyquinazoline Hydrochloride

A mixture of 4.8 g. (0.02 mole) of 4-amino-2-chloro-7,8-dimethoxyquinazoline and 4.5 g. (0.05 mole) of thiazolidine in 50 ml. of chlorobenzene is heated at reflux for 18 hours, cooled to room temperature and the precipitate collected by filtration to give the title compound which was purified by recrystallization.

B.
2-(3-Thiazolidinyl)-4-amino-7,8-dimethoxyquinazoline S-oxide

The product obtained in Part A, 1.0 g., is converted to the free base by partitioning between dilute aqueous sodium hydroxide and methylene chloride. The organic extracts are dried and concentrated in vacuo to 100 ml. To the methylene chloride solution of free base at 0° C. is added dropwise over 15 minutes a solution of 0.60 g. of m-chloroperbenzoic acid in 25 ml. of the same solvent. After stirring for 2 hours at 0° C. the reaction mixture is washed with dilute sodium bicarbonate and water. The organic extracts are dried (NaSO₄) and evaporated to dryness in vacuo to obtain the title S-oxide which purified by recrystallization, if desired.

The title compound is also obtained by the procedure of Part A, above, when thiazolidine-S-oxide is employed as starting material in place of thiazolidine.

C.
2-(3-Thiazolidinyl)-4-amino-7,8-dimethoxyquinazoline S,S-Dioxide

A mixture of 9.6 g. (0.04 mole) of 4-amino-2-chloro-7,8-dimethoxyquinoline and 10.0 g. of thiazolidine S,S-dioxide in 200 ml. of chlorobenzene is heated at reflux for 24 hours, cooled to room temperature and the product collected by filtration. The crude title compound is purified, if desired, by recrystallization.

D. Employing the above procedures or those of Examples 4, 8 or 17 the following compounds are similarly obtained from the appropriate starting materials.

[Structure: similar quinazoline with Y¹, Y², Y³ and NR¹R² substituents]

| Y¹ | Y² | Y³ | NR¹R² |
|---|---|---|---|
| H | CH₃O | CH₃O | N(CH₂)₂S(CH₂)₂ (thiazolidine ring) |
| Cl | CH₃O | H | N(CH₂)₂SO(CH₂)₂ (thiazolidine S-oxide ring) |

-continued

[Structure: benzamidine-type compound with Y¹, Y², Y³ substituents on the ring, NH₂ group, and NR¹R² group attached via N=C-N linkage forming quinazoline]

| Y¹ | Y² | Y³ | NR¹R² |
|---|---|---|---|
| Cl | CH₃O | CH₃O | N(CH₂)₂(CH₂)₂ with SO₂ bridge |
| H | CH₃O | CH₃O | N(CH₂)(CH₂)₃ with S bridge |
| Cl | CH₃O | H | N(CH₂)(CH₂)₃ with SO₂ bridge |
| Cl | CH₃O | CH₃O | N(CH₂)₂(CH₂)₃ with S bridge |
| H | C₂H₅O | C₂H₅O | N(CH₂)₂(CH₂)₃ with SO bridge |
| Cl | n-C₃H₇O | n-C₃H₇O | N(CH₂)₃(CH₂)₃ with S bridge |
| Cl | CH₃O | H | N(CH₂)₃(CH₂)₃ with SO₂ bridge |
| H | CH₃O | CH₃O | N(CH₂)(CH₂)₂ with O bridge, and (CH₂)₂ |
| Cl | CH₃ | CH₃O | N(CH₂)₂(CH₂)₂ with O bridge |
| Cl | CH₃O | H | N(CH₂)₃(CH₂)₃ with O bridge |

EXAMPLE 20

A.

2-(3-Hydroxypyrrolidin-1-yl)-4-amino-6-chloro-7,8-dimethoxyquinazoline hydrochloride A mixture of 4-amino-2,6-dichloro-7,8-dimethoxyquinazoline (5.48 g., 0.020 mole) and 3-pyrrolidinol (2.18 g., 0.025 mole) in 150 ml. of isoamyl alcohol is heated at reflux for five hours then cooled in ice. The precipitated product is collected by filtration and purified by recrystallization to obtain the title compound.

B.

2-[4-(2-Ethoxyethoxy)piperidin-1-yl]-4-amino-6-chloro-7,8-dimethoxyquinazoline hydrochloride 4-Amino-2,6-dichloro-7,8-dimethoxyquinazoline (4.9 g.), 4-(2-ethoxyethoxy)piperidine (3.2 g.) and triethylamine (10 ml.) in n-butanol (400 ml.) are heated at reflux overnight under an atmosphere of nitrogen. The mixture is then cooled, evaporated in vacuo, and the residue basified (aqueous Na₂CO₃) and extracted 3 times with chloroform. The combined chloroform extracts are evaporated and the residue chromatographed on neutral alumina to give the crude product which is converted to the hydrochloride salt by treatment with hydrogen chloride in ethanol to afford the title compound.

C.

By the above procedures the following compounds are similarly provided from the appropriate starting materials in each case.

[Structure: quinazoline with NH₂, Y¹, Y², Y³ substituents, and N-R¹R² group]

| Y¹ | Y² | Y³ | NR¹R² |
|---|---|---|---|
| H | CH₃O | CH₃O | N(CH₂)₂(CH₂)₂CHOH |
| Cl | CH₃O | CH₃O | N(CH₂)(CH₂)₃CHOCH₃ |
| Cl | CH₃O | CH₃O | N(CH₂)₃(CH₂)₃CHOCH₂(CH₂)₄CH₃ |
| H | CH₃O | CH₃O | N(CH₂)₂(CH₂)₂CHOC₆H₅ |
| H | CH₃O | CH₃O | N(CH₂)₂(CH₂)₃CHO(4-ClC₆H₄) |
| H | CH₃O | CH₃O | N(CH₂)(CH₂)₃CHO(2-BrC₆H₄) |
| Cl | CH₃O | H | N(CH₂)(CH₂)₃CHO—C₆H₄—CF₃ |
| Cl | CH₃O | H | N(CH₂)₂(CH₂)₂CHO(CH₂)₃OCH₃ |
| Cl | CH₃O | H | N(CH₂)₂(CH₂)₂CHOCH₂OCH₃ |
| Cl | CH₃O | H | N(CH₂)₂(CH₂)₂CHOCH₂CH₂S(CH₂)₃CH₃ |
| Cl | CH₃O | H | N(CH₂)₂(CH₂)₃CHOCH₂CH₂SC₆H₅ (with C=O) |
| Cl | CH₃O | H | N(CH₂)₂(CH₂)₂CHOCH₂CH₂SO₂-naphthyl, CH₃SO₂ substituent |

43
-continued

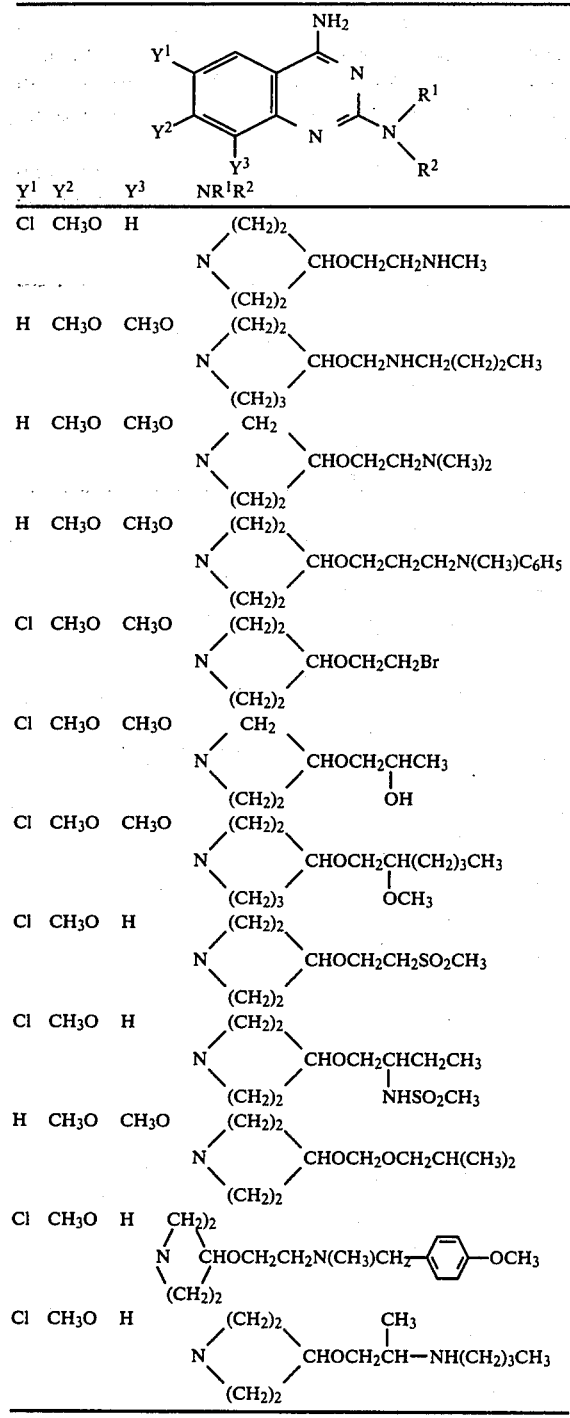

| Y¹ | Y² | Y³ | NR¹R² |
|---|---|---|---|
| Cl | CH₃O | H | N(CH₂)₂(CH₂)₂ CHOCH₂CH₂NHCH₃ |
| H | CH₃O | CH₃O | N(CH₂)₂(CH₂)₃ CHOCH₂NHCH₂(CH₂)₂CH₃ |
| H | CH₃O | CH₃O | N(CH₂)(CH₂)₂ CHOCH₂CH₂N(CH₃)₂ |
| H | CH₃O | CH₃O | N(CH₂)₂(CH₂)₂ CHOCH₂CH₂CH₂N(CH₃)C₆H₅ |
| Cl | CH₃O | CH₃O | N(CH₂)₂(CH₂)₂ CHOCH₂CH₂Br |
| Cl | CH₃O | CH₃O | N(CH₂)(CH₂)₂ CHOCH₂CHCH₃ OH |
| Cl | CH₃O | CH₃O | N(CH₂)₂(CH₂)₃ CHOCH₂CH(CH₂)₃CH₃ OCH₃ |
| Cl | CH₃O | H | N(CH₂)₂(CH₂)₂ CHOCH₂CH₂SO₂CH₃ |
| Cl | CH₃O | H | N(CH₂)₂(CH₂)₂ CHOCH₂CHCH₂CH₃ NHSO₂CH₃ |
| H | CH₃O | CH₃O | N(CH₂)₂(CH₂)₂ CHOCH₂OCH₂CH(CH₃)₂ |
| Cl | CH₃O | H | N(CH₂)₂(CH₂)₂ CHOCH₂CH₂N(CH₃)CH₂—⟨⟩—OCH₃ |
| Cl | CH₃O | H | N(CH₂)₂(CH₂)₂ CHOCH₂CH—NH(CH₂)₃CH₃ CH₃ |

EXAMPLE 21

A.
2-(Octamethyleneimin-1-yl)-4-amino-7,8-dimethoxyquinazoline hydrochloride To 500 ml. of isoamyl alcohol is added 23.9 g. (0.10 mole) 4-amino-2-chloro-7,8-dimethoxyquinazoline and 14.0 g. (0.11 mole) octamethyleneimine and the mixture is heated at reflux for 3.5 hours. After cooling, the precipitated solid is collected, washed with ether and dried to obtain the title compound.

44

B. By employing the above procedure with the appropriate starting materials in each case the following compounds are similarly provided.

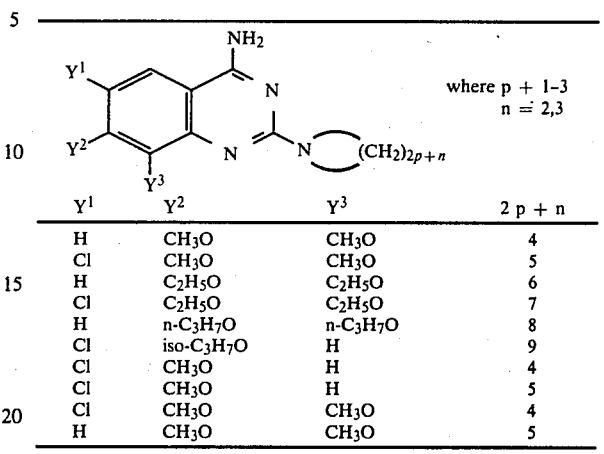

where p + 1–3
n = 2,3

| Y¹ | Y² | Y³ | 2p + n |
|---|---|---|---|
| H | CH₃O | CH₃O | 4 |
| Cl | CH₃O | CH₃O | 5 |
| H | C₂H₅O | C₂H₅O | 6 |
| Cl | C₂H₅O | C₂H₅O | 7 |
| H | n-C₃H₇O | n-C₃H₇O | 8 |
| Cl | iso-C₃H₇O | H | 9 |
| Cl | CH₃O | H | 4 |
| Cl | CH₃O | H | 5 |
| Cl | CH₃O | CH₃O | 4 |
| H | CH₃O | CH₃O | 5 |

EXAMPLE 22
2-(3-Methylpiperidin-1-yl)-4-amino-7,8-dimethoxyquinazoline

Equimolar amounts (0.10 mole) of 7,8-dimethoxy-2,4-(1H,3H)-quinazolinedione and phosphorous oxychloride are stirred at room temperature overnight and the volatiles evaporated in vacuo to afford a residue of 2-chloro-7,8-dimethoxy-4(3H)-quinazolineone which is purified by washing with aqueous sodium bicarbonate, extraction with chloroform and evaporation of solvent. To the residue is added a solution of 0.10 mole of 3-methylpiperadine in 300 ml. of isoamyl alcohol and the mixture heated at reflux for three hours, the solvent is then evaporated in vacuo to afford 2-(3-methylpiperidin-1-yl)-7,8-dimethoxy-4(3H)-quinazolineone hydrochloride. To this is added 150 ml. of phosphorous oxychloride and the resulting mixture is heated at reflux for two hours. The liquids are evaporated to give a residue of 2-(3-methylpiperidin-1-yl)-4-chloro-7,8-dimethoxyquinazoline hydrochloride. The product is dissolved in dilute aqueous sodium bicarbonate, extracted with chloroform, dried (Na₂SO₄) and the solvent evaporated.

The above product is dissolved in 350 ml. of tetrahydrofuran and a solution of anhydrous ammonia (5.3 g.) in the same solvent is added. The mixture is stirred at room temperature for 24 hours, the precipitate collected by filtration and purified by recrystallization to obtain the title compound.

EXAMPLE 23
2-(3-n-Hexylpyrrolidin-1-yl)-4-amino-6-chloro-7,8-dimethoxyquinazoline To 12 grams of 6-chloro-7,8-dimethoxy-2,4-(1H,3H)-quinazolinedione in 200 ml. of pyridine is added 30 g. of phosphorous pentasulfide and the mixture is refluxed with continuous stirring for five hours. The solvent is evaporated in vacuo and the residue decomposed with hot water. The solid material is filtered to obtain 6-chloro-7,8-dimethoxy-2,4-(1H,3H)-quinazolinedithione.

To 0.1 mole of 6-chloro-7,8-dimethoxy-2,4-(1H,3H)-quinazolinedithione in 220 ml. 1 N potassium hydroxide solution and 100 ml. methanol, is added slowly with stirring, 0.22 mole of methyl iodide. The mixture is heated on a steam bath for 2 hours, cooled, and the resulting precipitate is filtered from the mixture. The product is 6-chloro-2,4-dimethylmercapto-7,8-dimethoxyquinazoline.

To 0.1 mole of 6-chloro-2,4-dimethylmercapto-7,8-dimethoxyquinazoline in 200 ml. of tetrahydrofuan is added a solution of 0.1 mole of anhydrous ammonia in tetrahydrofuran. The mixture is stirred at room temperature for 18 hours and the precipitate which forms is collected and recrystallized from dimethylformamide/water to yield 2-methylmercapto-4-amino-6-chloro-7,8-dimethoxyquinazoline.

A mixture of 0.1 mole of 2-methylmercapto-4-amino-6-chloro-7,8-dimethoxyquinazoline and 0.12 mole of 3-n-hexylpyrrolidine in isoamyl alcohol is heated at reflux for 16 hours, cooled, washed with water and the organic phase is concentrated in vacuo. Hexane is slowly added to the residue and the solid title compound is collected and purified, if desired by silica gel column chromatography.

EXAMPLE 24

2-[4-(2,3-Dihydro-4H-benzopyran-2-carbonyl)-piperazin-1-yl]-4-amino-6-chloro-7-methoxyquinazoline hydrochloride To 0.10 mole of 2-(piperazin-1-yl)-4-amino-6-chloro-7-methoxyquinazoline in 300 ml. of methanol is added with vigorous stirring, 0.10 mole of 2,3-dihydro-4H-benzopyran-2-carboxylic acid chloride. After the addition is complete, the mixture is stirred for three hours at room temperature and the precipitated title compound is collected by filtration.

EXAMPLE 25

2-Diethylamino-4-amino-6-chloro-7-methoxyquinazoline

To 1.0 mole of 2,5-dichloro-4-methoxybenzonitrile in dimethylformamide (300 ml.) is added 0.5 mole of N,N-diethylguanidine and the mixture is heated at 150° C. for 12 hours. The solution is concentrated in vacuo to a small volume and poured into ice-water. The precipitated solid is collected by filtration and the crude product purified by silica gel column chromatography.

When 2-amino-5-chloro-4-methoxybenzontrile or 2-amidino-5-chloro-4-methoxyaniline is employed in the above reaction in place of 2,5-dichloro-4-methoxybenzonitrile the same compound is obtained.

EXAMPLE 26

2-(N-methyl-N-cyclohexylamino)-4-amino-6-chloro-7,8-dimethoxyquinazoline

A. To 5 liters of ethanol containing 0.2 mole of sodium ethoxide is added slowly with stirring 0.1 mole each of phenol and 2,4,6-trichloro-7,8-dimethoxyquinazoline. The mixture is heated to boiling then allowed to stand at room temperature overnight, poured into ice-water, stirred 15 minutes and the precipitate collected by filtration. The cake is washed with water, then cold ethanol, dried and recrystallized from ethanol/hexane to obtain 2,6-dichloro-7,8-dimethoxy-4-ethoxyquinazoline.

B. A mixture of 0.1 mole of the above product and 0.11 mole of N-methylcyclohexylamine in 350 ml. of ethanol is heated at reflux for three hours, cooled and poured into dilute aqueous sodium carbonate solution. The precipitated product is extracted with chloroform and the extracts evaporated to dryness to obtain 2-(N-methyl-N-chlorohexylamino)-4-ethoxy-7,8-dimethoxyquinazoline suitable for use in the next step.

C. To 0.1 mole of the product of Part B in 300 ml. of tetrahydrofuran, anhydrous ammonia is passed through until the mixture has absorbed 0.11 mole. The mixture is then stirred for 24 hours at room temperature, then heated at reflux for two hours and cooled in ice. The precipitated solid is collected by filtration to afford the title compound which may be purified, if desired, by recrystallization or by chromatography.

D. When 2,6-dichloro-7,8-dimethoxy-4-methyl-thioquinazoline (prepared from the corresponding 2,4,6-trichloro- compound and methylmercaptan in the presence of sodium ethoxide by the procedure of Curd et al., J. Chem. Soc., 775–783 (1947) for 2-chloro-4-methylthioquinazoline) is used in place of 2,6-dichloro-7,8-dimethoxy-4-ethoxyquinazoline in Part B, above, and the resulting product carried through the above procedures the title compound is similarly obtained.

EXAMPLE 27

2-(Morpholin-4-yl)-4-amino-7,8-dimethoxyquinazoline hydrochloride

To 500 ml. of methylethylketone is added 0.1 mole of 4-amino-2-chloro-7,8-dimethoxyquinazoline and 0.12 mole of morpholine and the mixture is refluxed overnight. After cooling in ice-water the solid precipitated is collected by filtration, washed with ether and air dried to obtain the title compound.

When the appropriate starting materials are employed in each case in the above procedure or any of the procedures of Examples 17, or 22–26, the following compounds are likewise obtained.

| $Y^1$ | $Y^2$ | $Y^3$ | m | n |
|---|---|---|---|---|
| H | $CH_3O$ | $CH_3O$ | 2 | 3 |
| Cl | $C_2H_5O$ | $CH_3O$ | 2 | 2 |
| Cl | $n-C_3H_7O$ | H | 3 | 3 |
| Cl | $CH_3O$ | H | 2 | 2 |
| Cl | $CH_3O$ | H | 2 | 3 |
| Cl | $CH_3O$ | $CH_3O$ | 2 | 3 |
| H | $CH_3O$ | $CH_3O$ | 3 | 3 |
| Cl | $C_2H_5O$ | $C_2H_5O$ | 3 | 3 |

EXAMPLE 28

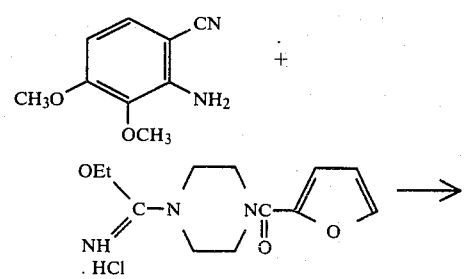

-continued

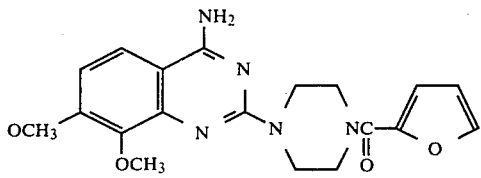

To a stirred solution of 1.78 g. (0.01 mole) 3,4-dimethoxy-2-aminobenzonitrile in 30 ml. of N,N-dimethylformamide is added 2.88 g. (0.01 mole) ethyl 4-(2-furoyl)piperazin-1-ylformimidate hydrochloride followed by 855 mg. (0.02 mole) of a 56.1% dispersion of sodium hydride in mineral oil. The reaction mixture is stirred at ambient temperature for 30 minutes, and then it is heated to ca. 100° C. and maintained at that temperature for 12 hours. The reaction mixture is cooled to ambient temperature, diluted with an excess of water, and then extracted with chloroform. The chloroform extract is washed several times with water, dried using anhydrous magnesium sulfate, and then evaporated to dryness in vacuo. This affords crude 7,8-dimethoxy-4-amino-2-[4-(2-furoyl)piperazin-1-yl]quinazoline, which is purified further by recrystallization from aqueous ethanol.

B. The above procedure is repeated, except that the ethyl 4-(2-furoyl)piperazin-1-ylformimidate hydrochloride used therein is replaced by an equimolar amount of:

ethyl 4-allylpiperazin-1-ylformimidate methanesulfonate, methyl 4-benzoylpiperazin-1-ylformimidate hydrochloride, isopropyl 4-(3-furoyl)piperazin-1-ylformimidate hydrochloride, methyl 4-(allyloxycarbonyl)piperazin-1-ylthioformimidate hydroiodide, ethyl 4-(2-methylprop-2-enyloxycarbonyl)piperazin-1-ylthioformimidate hydrobromide and ethyl-4-(2-hydroxy-2-methylprop-1-yloxycarbonyl)piperazin-1-ylthioformimidate hydrobromide, respectively.

This affords:

7,8-dimethoxy-4-amino-2-(4-allylpiperazin-1-yl)quinazoline, 7,8-dimethoxy-4-amino-2-(4-benzoylpiperazin-1-yl)quinazoline, 7,8-dimethoxy-4-amino-2-[4-(3-furoyl)piperazin-1-yl]quinazoline, 7,8-dimethoxy-4-amino-2-[4-(allyloxycarbonyl)piperazine-1-yl]quinazoline, 7,8-dimethoxy-4-amino-2-[4-(2-methylprop-2-enyloxycarbonyl)piperazin-1-yl]quinazoline and 7,8-dimethoxy-4-amino-2-[4-(2-hydroxy-2-methylprop-1-yloxycarbonyl)piperazin-1-yl]quinazoline, respectively, C. The procedure of Part A is repeated, except that the 3,4-dimethoxy-2-aminobenzonitrile used therein is replaced by an equimolar amount of:

5-chloro-3,4-dimethoxy-2-aminobenzonitrile,

5chloro-3,4-diethoxy-2-aminobenzonitrile, 5-chloro-4-methoxy-2-aminobenzonitrile, or 5-chloro-4-isopropoxy-2-aminobenzonitrile, to provide the following compounds, respectively,

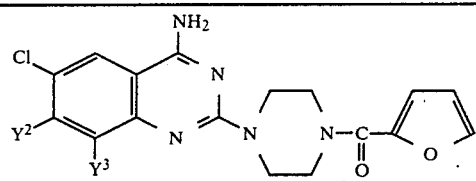

| $Y^2$ | $Y^3$ |
|---|---|
| $CH_3O$ | $CH_3O$ |
| $C_2H_5O$ | $C_2H_5O$ |
| $CH_3O$ | H |
| $(CH_3)_2CHO$ | H |

EXAMPLE 29

5-Chloro-4-methoxy-2-aminobenzamidine hydrochloride prepared by the procedure of U.S. Pat. No. 3,935,213 for analogous compounds (0.01 mole) and an equimolar amount of 1-cyano-4-ethoxycarbonylpiperazine also provided in the same reference, are dissolved in 50 ml. of anhydrous ethanol and stirred overnight at ambient temperature. A 5 ml. aliquot of triethylamine is added and the mixture is heated at reflux for 12 hours. The solvent is evaporated to provide 4-amino-6-chloro-7-methoxy-2-[4-ethoxycarbonylpiperazin-1-yl]quinazoline as the hydrochloride salt.

EXAMPLE 30

A stirred solution of 24 ml. of concentrated sulfuric acid dissolved in an equal volume of water was cooled to 10°–12° C. and 0.015 mole of methallyl 4-(4-amino-6-chloro-7,8-dimethoxyquinazolin-2-yl)piperazine-1-carboxylate is added in small portions with stirring. The addition is carried out at a rate sufficient to keep the reaction temperature below 20° C. The resulting mixture is stirred for 15 minutes at 15°–20° C., then for two hours at 10°–15° C. The reaction mixture is diluted with 150 ml. of ice-water and adjusted to pH 10 with sodium hydroxide while maintaining the temperature below 12° C. After extraction with chloroform, the combined extracts are washed with water and dried over anhydrous sodium sulfate. The solvent is evaporated in vacuo and the residue recrystallized to afford 2-methyl-2-hydroxypropyl 4-(4-amino-6-chloro-7,8-dimethoxyquinazolin-2-yl)piperazine-1-carboxylate.

EXAMPLE 31

2-[4-(3-hydroxypropyl)homopiperazin-1-yl]-4-amino-7,8-dimethoxyquinazoline hydrochloride A. 2-Chloro-4-amino-7,8-dimethoxyquinazoline, 17 g. and N-formylhomopiperazine, 18.2 g. are added to 170 ml. n-butanol and the mixture is refluxed for three hours, cooled and the precipitated solid collected by filtration. The precipitate is washed with a small amount of ethanol and air-dried. A mixture of 13 g. of this solid and 80 ml. of 9% (by weight) hydrochloric acid are heated at reflux for 60 minutes, then allowed to cool and the precipitate of 2-homopiperazino-4-amino-7,8-dimethoxyquinazoline is collected and purified, if desired, by recrystallization.

B. A mixture of 4 g. of triethylamine, 3.0 g. of 2-homopiperazino-4-amino-7,8-dimethoxyquinazoline, 4.5 g. of 3-bromo-1-propanol and 50 ml. of diethyleneglycol dimethylether is heated at 100°–120° C. with stirring for 16 hours. The reaction mixture is concentrated in vacuo and the residue made alkaline by addition of sodium hydroxide solution. The mixture is extracted with chloroform, the extracts washed with water, dried with potassium carbonate and filtered. The filtrate is concentrated, the residue taken up in isopropanol and a solution of hydrogen chloride in isopropanol added until precipitation is complete. The title compound is collected by filtration and dried.

C. When an equivalent amount of 1,3-propandiol monotosylate or 1,3-propandiol monomethylsulfonate are employed in place of 3-bromo-1-propanol in Part B, above, the results are substantially the same.

EXAMPLE 32

Employing the appropriate starting materials in each case the following compounds are prepared by the procedures of Examples 31 according to the equation

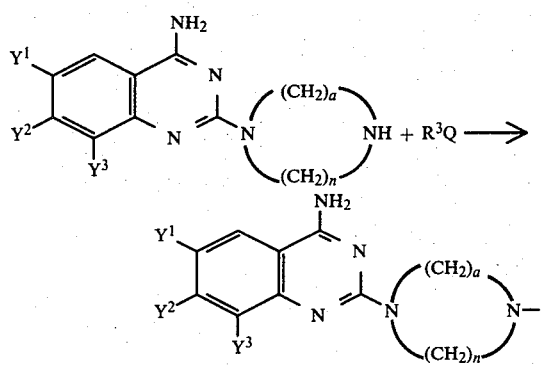

Where a is 1 or m; m and n are 2 or 3 and Q is a leaving group such as Br, Cl, p-toluenesulfonyloxy or methanesulfonyloxy.

| $Y^1$ | $Y^2$ | $Y^3$ | a | n | $R^3$ |
|---|---|---|---|---|---|
| Cl | $CH_3O$ | H | 1 | 2 | $CH_3$ |
| Cl | $CH_3O$ | $CH_3O$ | 1 | 3 | $CH_3(CH_2)_3$ |
| H | $C_2H_5O$ | $C_2H_5O$ | 2 | 2 | $(CH_3)_2CH(CH_2)_3$ |
| Cl | $C_2H_5O$ | H | 2 | 2 | $CH_3(CH_2)_5$ |
| Cl | $n-C_3H_7O$ | $n-C_3H_7O$ | 2 | 2 | $CH_2=CHCH_2$ |
| H | $i-C_3H_7O$ | $i-C_3H_7O$ | 3 | 2 | $CH_3CH=CHCH_2$ |
| Cl | $CH_3O$ | H | 3 | 2 | $(CH_3)_2C=CHCH_2$ |
| Cl | $CH_3O$ | $CH_3O$ | 3 | 3 | $HC\equiv C-CH_2$ |
| H | $CH_3O$ | $CH_3O$ | 3 | 3 | $CH_3C\equiv CCH_2$ |
| Cl | $CH_3O$ | $CH_3O$ | 1 | 2 | $HOCH_2CH_2$ |
| Cl | $CH_3O$ | H | 2 | 2 | $(CH_3)_2C(OH)CH_2$ |
| H | $CH_3O$ | $CH_3O$ | 1 | 2 | $(CH_3)_2C(OH)CH_2CH_2$ |
| Cl | $CH_3O$ | H | 2 | 2 | cyclopropyl |
| Cl | $CH_3O$ | $CH_3O$ | 2 | 3 | cyclopentyl |
| H | $CH_3O$ | $CH_3O$ | 3 | 3 | cyclohexyl |
| Cl | $CH_3O$ | H | 2 | 2 | cycloheptyl |
| Cl | $CH_3O$ | $CH_3O$ | 2 | 2 | cyclooctyl |
| H | $CH_3O$ | $CH_3O$ | 2 | 3 | 1-naphthyl |
| H | $CH_3O$ | $CH_3O$ | 2 | 2 | 2-naphthylmethyl |
| H | $CH_3O$ | $CH_3O$ | 2 | 2 | $4-HOC_6H_5$ |
| H | $CH_3O$ | $CH_3O$ | 2 | 2 | $4-BrC_6H_4CH_2$ |
| H | $CH_3O$ | $CH_3O$ | 1 | 2 | $3-CH_3C_6H_4CH_2$ |
| Cl | $CH_3O$ | $CH_3O$ | 1 | 3 | 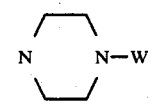 NHSO₂CH₃ |
| H | $CH_3O$ | $CH_3O$ | 2 | 3 | CH₃ 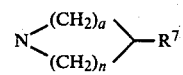 |
| H | $CH_3O$ | $CH_3O$ | 2 | 2 | OH ...CH₂ |
| H | $CH_3O$ | $CH_3O$ | 1 | 2 | CF₃—...—CH₂ |

EXAMPLE 33

A. 2,3-Dimethoxyaniline obtained by the method of Gibson et al., *J. Chem. Soc.*, 111, 79 (1917), is converted to 2,3-dimethoxy isothiocyanate according to the procedure of Dyson et al, *J. Chem. Soc.*, 436 (1927) for analogous compounds.

A solution of 2,3-dimethoxy isothiocyanate (32.1 g., 0.164 mole) in 100 ml. of absolute ethanol is added to a stirred solution of 1-(2-furoyl)piperazine (29.6 g., 0.164 mole) prepared by the method of Desai et al., *Org. Prep. Proced. Int.*, 8, 85 (1976) in 350 ml. of absolute ethanol and the mixture heated at reflux for 2.5 hours. The crude 4-(2-furoyl)piperazine-1-(N-2,3-dimethoxyphenyl)carbothioamide is isolated by evaporation of solvent in vacuo and purified by recrystallization.

B. To a suspension of 22.0 g. (0.0586 mole) of the product obtained in Part A, above, in 400 ml. of methanol is added methyl iodide 8.32 g. (0.0586 mole). The mixture is stirred at reflux for 2.5 hours, cooled to 20° C., 18.7 g. of cyanamide (0.445 mole) is added and the resulting mixture is heated at reflux for an additional 16 hours. The solvent is evaporated in vacuo and the residue made strongly basic with 4.0 N sodium hydroxide. The alkaline mixture is extracted with chloroform, the extracts washed first with water then with saturated brine and dried over anhydrous magnesium sulfate. The dried extract is concentrated to dryness under reduced pressure and the residue crystallized to afford 4-(2-furoyl)piperazine-1-[N-cyano-N'-(2,3-dimethoxyphenyl)]carboxamidine.

C. Following the procedure of Part A, above, but employing an equimolar amount of 2,3-dimethoxyphenyl isocyanate in place of 2,3-dimethoxyphenyl isothiocyanate, there is obtained N-(2,3-dimethoxyphenyl)-4-(2-furoyl)-1-piperazinecarboxamide. Reaction of this carboxamidee with methyl fluorosulfonate and then with cyanamide according to the procedure of Part B, above, provides the same product obtained in Part B.

D. By employing other amines of formula $R^1R^2NH$, where $R^1$ and $R^2$ are as shown in Examples 18 and 19 or taken together $R^1$ and $R^2$ are $$N\diagdown\diagup N-W$$

as in Examples 10 and 16 or $$N{\diagdown}{(CH_2)_a \atop (CH_2)_n}{\diagup}R^7$$

as in Example 14, in the procedures of Parts A and B or Part C, above, provides compounds of the following formula in like manner.

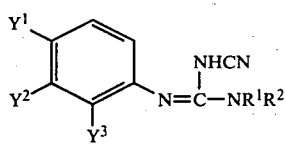

$Y^1$, $Y^2$, $Y^3$ have the values shown in Examples 10, 14, 16, 18 and 19.

EXAMPLE 34

4-Amino-7,8-dimethoxy-2-[4-(2-furoyl)piperazin-1-yl]quinazoline hydrochloride A. To 10 ml. of phosphorus oxychloride is added with stirring 0.31 g. of phosphorus pentachloride (1.48 mmoles) followed by 0.54 g. (1.48 mmoles) of 4-(2-furoyl)piperazine-1[N-cyano-N'-(2,3-dimethoxyphenyl)]carboxamidine of Example 33, Part B. The reaction mixture is heated at 95°–98° C. for 2.5 hours, cooled to 30° C. and excess phosphorus oxychloride is evaporated in vacuo and the residue is triturated with ice water. The aqueous phase is filtered and the filtrate concentrated in vacuo to provide the crude product which is purified by crystallization or column chromatography.

B. When the phosphorus pentachloride used above is replaced by an equimolar amount of hydrogen chloride gas, phosphorus pentabromide, trifluoroacetic acid, $ZnCl_2$, $FeCl_3$, $AlCl_3$ or $AlBr_3$ and the reaction carried out at 70°–100° C. for one to three hours the results are substantially the same as in Part A.

EXAMPLE 35

Tablets

A tablet base is prepared by blending the following ingredients in the proportion by weight indicated:

| Sucrose, U.S.P. | 80.3 |
|---|---|
| Tapioca starch | 13.2 |
| Magnesium stearate | 6.5 |

Into this base is blended sufficient 2-[4-(2-furoyl)-1-piperazinyl]-4-amino-6-chloro-7-methoxyquinazoline hydrochloride to provide tablets containing 0.5, 1.0, 10, 100 and 250 mg. of active ingredient.

EXAMPLE 26

Capsules

A blend is prepared containing the following ingredients:

| Calcium carbonate, U.S.P. | 17.6 |
|---|---|
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 2-[4-(2-hydroxy-2-methylprop-1-yloxycarbonyl)piperazin-1-yl]-4-amino-6-chloro-7-methoxyquinazoline to provide formulations containing 0.5, 1.0, 5, 10, 100, 250 and 500 mg. of active ingredient, and the formulations are filled into hard gelatin capsules of a suitable size.

EXAMPLE 37

Injectable Preparation

2-[4-(2-furoyl-1-piperazinyl]-4-amino-6,7-dimethoxyquinazoline hydrochloride is intimately mixed and ground with 2500 g. of sodium ascorbate. The ground dry mixture is filled into vials, sterilized with ethylene oxide and the vials sterile stoppered. For intravenous administration sufficient water is added to the vials to form a solution containing 10 mg. of active ingredients per milliliter.

EXAMPLE 38

Solution

A solution of 2-[4-(2-hydroxy-2-methylprop-1-yloxycarbonyl)piperazin-1-yl]-4-amino-6-chloro-7,8-dimethoxyquinazoline or a pharmaceutically acceptable salt thereof is prepared with the following composition:

| Effective ingredient | 30.22 g. |
|---|---|
| Magnesium chloride hexahydrate | 12.36 g. |
| Monoethanolamine | 8.85 ml. |
| Propylene glycol | 376 g. |
| Water | 94 ml. |

The solution has a concentration of 50 mg./ml. and is suitable for parenteral and especially for intramuscular administration.

PREPARATION A

4-Acetoxy-3-methoxybenzaldehyde (IV)

Triethylamine (2.8 liters, 20.1 moles) was added dropwise to a solution of vanillin (2.00 kg., 13.15 moles) and acetic anhydride (2.6 liters, 27.5 moles) in methylene chloride (11.3 liters) maintaining temperature below 25° C. After adding 4-dimethylaminopyridine (20 g.) the solution was stirred at room temperature for 30 minutes. The reaction mixture was washed twice with water, followed by 20% (w/w) hydrochloric acid and brine. The organic layer was dried over sodium sulfate and concentrated in vacuo to 8 liters. Hexane (15 liters) was added slowly while removing remaining methylene chloride. After cooling, 2.45 kg. (96% yield) product was filtered off. Recrystallization of a small sample from anhydrous ether gave the acetate as fine yellow needles, M.P. 76°–78° C.

PREPARATION B

4-Acetoxy-3-methoxy-2-nitrobenzaldehyde (V)

Over a period of 1.5 hours 4-acetoxy-3-methoxybenzaldehyde (1120 g., 5.77 moles) was added in small portions to 4 liters of red fuming nitric acid cooled to 0° C. After allowing to stir for one hour below 5° C., the reaction mixture was added to large amount of icewater and stirred an additional hour. The resulting yellow product (1130 g., 82% yield) was filtered and washed three times with water, and was sufficiently pure for use directly in the next step. Recrystallization from ether/cyclohexane furnished the pure nitroaldehyde, M.P. 84°–86° C.

PREPARATION C

4-Hydroxy-3-methoxy-2-nitrobenzaldehyde (VI)

4-Acetoxy-3-methoxy-2-nitrobenzaldehyde (1120 g., 4.72 moles) was added portionwise to a freshly prepared 33% (w/w) NaOH solution (4.5 liters). The resulting slurry was heated on steam bath at 75° C. for 10 minutes after which it was diluted with 5 liters of water. The reaction mixture was acidified with 6.4 liters of 6 N hydrochloric acid while cooling, and the resulting product (794 g., 85% yield) was filtered and washed with water. Recrystallization from ether/cyclohexane gave the desired product as light yellow solid, M.P. 136°-137° C.

PREPARATION D i. 3,4-Dimethoxy-2-nitrobenzaldehyde (VII)

Anhydrous sodium carbonate (957 g., 9.03 moles), toluene (5 liters), 4-hydroxy-3-methoxy-2-nitrobenzaldehyde (1424 g., 7.22 moles) and dimethyl sulfate (810 ml., 8.67 moles) were refluxed for 4 hours. Toluene was removed in vacuo and the residual solid dissolved in 5 liters of ethyl acetate and 3 liters of water. The organic layer was separated, washed with 2 liters of 1 N NaOH and 6 liters of brine, decolorized with charcoal, dried over magnesium sulfate and filtered. Hexane (7.6 liters) was added slowly. After cooling in an ice bath, 1527 g. product was obtained by filtration. The crude material was recrystallized from ethanol to yield 1187 g. (78%) of the title compound as a pale yellow solid, 60°-62° C.

ii. By employing diethyl sulfate in place of dimethyl sulfate in the above procedure, 4-ethoxy-3-methoxy-2-nitrobenzaldehyde is similarly obtained.

iii. When n-propyl bromide is employed as the alkylating agent the corresponding 4-n-propyloxy compound is provided.

PREPARATION E 3,4-Dimethoxy-2-nitro-benzoic acid (VIII)

A solution of 823 g. potassium permanganate in about 8.5 liters of $H_2O$ was gradually added to a refluxing solution of 3,4-dimethoxy-2-nitrobenzaldehyde (550 g., 2.60 moles) in 5.6 liters of acetone. The reaction mixture was refluxed for four more hours, then filtered through diatomaceous earth while hot and the filter cake washed with hot water. The acetone was removed in vacuo and a small amount of unreacted solid was filtered off. The aqueous solution was acidified with 2 N hydrochloric acid (1.8 liters) to yield 505 g. (85%) of the essentially pure title compound. Recrystallization from water afforded colorless crystals, M.P. 200°-202° C.

PREPARATION F 3,4-Dimethoxyanthranilic acid (IXa, R=CH₃)

A solution of 3,4-dimethoxy-2-nitro benzoic acid (1011 g., 4.45 moles) in 14 liters of 1.3 N ammonium hydroxide was reduced at 60 psi in presence of 60 grams of palladium on barium carbonate. Hydrogen uptake ceased after four hours. The reaction mixture was filtered through diatomaceous earth and acidified with glacial acetic acid (1.2 liters) to yield 685 grams (78%) of the anthranilic acid, M.P. 183°-184° C.

PREPARATION G

4-Methoxy anthranilic acid (XXII)

i. 4-Cyano-3-nitroanisole (XIX)

A saturated solution of sodium nitrite (33.5 g., 0.485 mole) was added dropwise to a cooled solution of 4-methoxy-2-nitroaniline (68.0 g., 0.404 mole) in 300 ml. water and 94 ml. concentrated hydrochloric acid, while maintaining the temperature at 0° C. and the pH at 6 by addition of sodium carbonate.

The cold solution of diazonium salt was added carefully through a jacketed dropping funnel to a hot solution of cuprous cyanide (36.2 g., 0.404 mole) and potassium cyanide (42.1 g., 0.646 mole) in 500 ml. water, with vigorous stirring and intermittent heating on a steambath. The stirred yellow suspension was heated an additional fifteen minutes. The solid was filtered, dried and dissolved in ethyl acetate, discarding the undissolved inorganic salts. After decolorization with charcoal, concentration of the ethyl acetate solution yielded 55.1 g. (71%) of bright yellow-orange crystals, M.P. 135°-7° C.

Analysis, Percent Calc'd for $C_8H_6N_2O_3$: C, 53.93; H, 3.39; N, 15.73 Found: C, 53.92; H, 3.47; N, 15.85.

ii. 4-Methoxy-2-nitrobenzoic acid (XXI)

4-Cyano-3-nitroanisole (52.3 g., 0.294 mole) was slowly added to a cooled solution of 53 ml. each of acetic acid, water and sulfuric acid. The solution was refluxed for 5 hours, and then diluted with 160 ml. water. After cooling, the resulting solid was filtered and dissolved in 10% sodium hydroxide solution. After decolorization with charcoal the solution was acidified with 6 N HCl, cooled and the yellow product (51.0 g., 88% yield) was filtered. An analytical sample was recrystallized from methanol/water, M.P. 196°-7° C.

Analysis, Percent Calc'd for $C_8H_7NO_5$: C, 48.74; H, 3.58; N, 7.11 Found: C, 48.37; H, 3.57; N, 7.03.

iii. 4-Methoxy anthranilic acid (XXII)

A solution of 4-methoxy-2-nitrobenzoic acid (19.3 g., 97.9 mmole) in 200 ml. 1 N $NH_4OH$ was reduced overnight in presence of 5% $Pd/BaCO_3$. The reaction mixture was filtered and acidified with acetic acid to yield 15.8 g. (96%) of the anthranilic acid, M.P. 186°-188° C.

iv. Employing 4-ethoxy-2-nitroaniline or the corresponding 4-n-propoxy- or 4-isopropoxy- compounds as starting material in the above procedures the following products are similarly obtained.

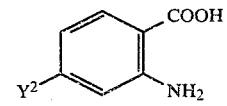

where $Y^2$ is ethoxy, n-propoxy or isopropoxy.

PREPARATION H i. Methyl-3,4-dimethoxyanthranilate

Hydrogen chloride was passed into a solution of 3,4-dimethoxyanthranilic acid (100 g., 0.51 mole) in 1.5 liters methanol for 40 minutes. The reaction mixture was refluxed for 4 days while introducing hydrogen chloride gas intermittently. The solvent was removed in vacuo, and the residual white solid was dissolved in 500 ml. water, cooled and basified to pH 10 with sodium hydroxide solution. After cooling for an additional hour, the cream color product (87.0 g., 82% yield) was filtered. Recrystallization from methanol furnished pure product, M.P. 66°-67° C.

Analysis, Percent Calc'd for $C_{10}H_{13}NO_4$: C, 56.86; H, 6.20; N, 6.63 Found: C, 56.56; H, 6.15; N, 6.66.

ii. Methyl-4-methoxyanthranilate

Esterification of 4-methoxy anthranilic acid as described above afforded methyl-4-methoxyanthranilate, M.P. 77°-79° C., in 77% yield.

PREPARATION I i. 5-Chloro-3,4-dimethoxyanthranilic acid (IXb, R=CH$_3$)

Sulfuryl chloride (19.3 ml., 0.24 mole) was added dropwise to a cooled solution of methyl 3,4-dimethoxyanthranilate (42.2 g., 0.20 mole) in 400 ml. chloroform at 0° C. (The sulfur dioxide produced was passed through a water trap). After stirring 30 minutes at ambient temperature the solution was refluxed for 2 hours. The black solution was treated with charcoal and the solvent was evaporated. The $^1$H-NMR spectrum indicated that the black, oily residue was largely the desired intermediate ester. The crude methyl ester was saponified with 400 ml. 5% (w/v) sodium hydroxide on a steam bath for one hour. After cooling, the basic suspension was acidified with acetic acid to precipitate a brown solid which was filtered and recrystallized from carbon tetrachloride to afford light-brown crystalline product (29.0 g., 63.1% yield), M.P. 140°-2° C. [Reported M.P. 142°-3° C., *J. Chem. Soc.*, 4310-4, 1964].

Analysis, Percent Calc'd. for C$_9$H$_{10}$ClNO$_4$: C, 46.66; H, 4.35; N, 6.05 Found: C, 46.45; H, 4.45; N, 5.90.

ii. 5-chloro-4-methoxyanthranilic acid (IXc, R=CH$_3$)

Treatment of methyl-4-methoxyanthranilate with sulfuryl chloride as described above afforded methyl-4-methoxy-5-chloroanthranilate, M.P., 197°-200° C. in 90% yield.

Saponification of methyl-4-methoxy-5-chloro anthranilate yielded 5-chloro-4-methoxyanthranilic acid in 64% yield, M.P., 210°-3° C.

Analysis, Percent Calc'd for C$_8$H$_8$ClNO$_3$: C, 47.66; H, 4.00; N, 6.95 Found: C, 48.00; H, 4.11; N, 6.94.

When methyl 4-ethoxyanthranilate or methyl 4-n-propyloxyanthranilate are carried through the above procedure 5-chloro-4-ethoxyanthranilic acid and 5-chloro-4-n-propyloxyanthranilic acid are obtained in like manner.

PREPARATION J

When ethyl vanillin (3-ethoxy-4-hydroxybenzaldehyde) or propyl vanillin, (4-hydroxy-3n-propyloxybenzaldehyde) are employed as starting material in the procedure of Preparation A in place of vanillin and the resulting products carried in turn, through the procedures of Preparation B-F and optionally chlorination by the procedures of Preparations H and I, the corresponding compounds of the following formula are similarly obtained.

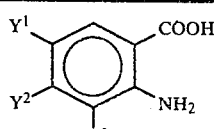

| Y$^1$ | Y$^2$ | Y$^3$ | Y$^1$ | Y$^2$ | Y$^3$ |
|---|---|---|---|---|---|
| H | C$_2$H$_5$O | C$_2$H$_5$O | Cl | C$_2$H$_5$O | C$_2$H$_5$O |
| H | n-C$_3$H$_7$O | n-C$_3$H$_7$O | Cl | n-C$_3$H$_7$O | n-C$_3$H$_7$O |
| H | CH$_3$O | C$_2$H$_5$O | Cl | CH$_3$O | C$_2$H$_5$O |
| H | n-C$_3$H$_7$O | CH$_3$O | Cl | C$_2$H$_5$O | CH$_3$O |
| H | C$_2$H$_5$O | CH$_3$O | Cl | n-C$_3$H$_7$O | CH$_3$O |
| H | n-C$_3$H$_7$O | C$_2$H$_5$O | Cl | n-C$_3$H$_7$O | C$_2$H$_5$O |

PREPARATION K 3-(m-Trifluoromethylphenyl)piperidine i. N-Benzyl-3-hydroxy-3-(m-trifluoromethylphenyl)piperidine Under anhydrous conditions, to a mixture of 11 g. of magnesium in 15 ml. of ethyl ether an iodine crystal is added followed by the addition of a solution of 100 g. of m-bromotrifluoromethylbenzene in 300 ml. of ether over a two hour period. The resulting mixture is stirred for two hours at ambient temperature then cooled to 5° C. A solution of 70 g. of N-benzyl-3-piperidone in 300 ml. of ether is added at this temperature over one hour. After stirring for 15 minutes at 5° C. and one hour at 20°-25° C., the reaction mixture was poured onto 800 ml. of ice-water with stirring. The mixture is filtered, the organic layer extracted with 4×100 ml. of 1 N hydrochloric acid and once with brine. The aqueous phase is made alkaline by addition of triethylamine in the cold and the resulting mixture extracted with ethyl acetate. The combined extracts are washed with brine, dried (MgSO$_4$) and evaporated to dryness. The crude product is purified by silica gel chromatography, eluting with cyclohexane/chloroform/triethylamine (85:10:5 by volume) to obtain the desired product as an orange colored solid.

ii. N-Benzyl-3-acetoxy-3-(m-trifluoromethylphenyl)piperidine hydrochloride

A mixture of 37 g. of N-benzyl-3-hydroxy-3-(m-trifluoromethylphenyl)piperidine, 220 ml. of acetic anhydride and 0.3 ml. of concentrated sulfuric acid is heated to 110° C. for one hour. After cooling it is poured onto ice-water, the resulting mixture agitated for 15 minutes and made alkaline by addition of sodium hydroxide solution. The mixture is extracted with ethyl acetate, the extracts washed with brine, dried (MgSO$_4$) and evaporated to dryness to obtain 39 g. of the free base. This is dissolved in 600 ml. of ethyl acetate, cooled in ice, and 100 ml. of ethanol saturated with hydrogen chloride is added. The solvent is removed by evaporation in vacuo and the residue triturated with 200 ml. of ethyl acetate then 200 ml. of ethyl ether is added and the mixture allowed to stand overnight. The crystalline title compounds is collected by filtration, washed with ether and dried to obtain 36 g., M.P. 206°-207° C.

iii. The product obtained in Part ii is dissolved in 700 ml. of ethanol. Palladium-on-carbon catalyst (40 g). is added and the mixture hydrogenated at room temperature. When hydrogen uptake ceases the catalyst is removed by filtration and solvent evaporated in vacuo. The resulting solid is washed with ether and dried to obtain 21 g. of 3-(m-trifluoromethylphenyl)piperidine hydrochloride as colorless crystals, M.P. 200° C.

iv. Employing the appropriate cyclic aminoketone, selected from N-benzyl-3-pyrrolidone, N-benzyl-3-piperidine, N-benzyl-4-piperidone, N-benzyl-4-oxo-azacycloheptane and N-benzyl-4-oxo-azacyclooctane, and the appropriate R$^7$Hal (where Hal is Cl, Br or I) in the above procedure the following compounds are obtained in similar manner.

$$\begin{array}{c} \text{HN} \overset{(CH_2)_a}{\underset{(CH_2)_n}{\diagup\hspace{-0.3em}\diagdown}} \text{CHR}^7 \end{array}$$

| a | n | R⁷ |
|---|---|-----|
| 1 | 2 | CH₃ |
| 1 | 2 | CH₃(CH₂)₅ |
| 1 | 2 | (CH₃)₂CH—CH₂ |
| 1 | 2 | C₆H₅ |
| 1 | 2 | C₆H₄CH₂ |
| 1 | 2 | 4-ClC₆H₄CH₂ |
| 1 | 2 | 3-CH₃C₆H₄ |
| 1 | 3 | (CH₃)₂CH |
| 1 | 3 | CH₃(CH₂)₄ |
| 1 | 3 | 3-FC₆H₄ |
| 1 | 3 | 4-CH₃OC₆H₄CH₂ |
| 2 | 2 | 4-HOC₆H₄ |
| 2 | 2 | 3-CH₃SO₂C₆H₄ |
| 2 | 2 | 2-CH₃SO₂NHC₆H₄CH₂ |
| 2 | 3 | CH₃CH₂ |
| 2 | 3 | 4-CH₃SO₂NHC₆H₄ |
| 2 | 3 | CH₃(CH₂)₃ |
| 2 | 3 | 4-CF₃C₆H₄CH₂ |
| 2 | 3 | 4-FC₆H₄ |
| 3 | 3 | CH₃ |
| 3 | 3 | C₆H₅ |
| 3 | 3 | C₆H₅CH₂ |
| 3 | 3 | 4-CH₃C₆H₄ |
| 3 | 3 | 3-CH₃OC₆H₄ |

PREPARATION L i. 3-Benzoylpiperidine hydrochloride

The method is that of U.S. Pat. No. 3,576,810. To 500 ml. of thionyl chloride was added 85.6 g. (0.5 mole) of 1-acetylnipecotic acid. The stirred mixture was heated at ca. 60° C. for two hours and then the solvent was evaporated at reduced pressure. The crude acid chloride was taken up in 200 ml. of dry benzene and the resulting solution added slowly to a mixture of 133 g. (1.0 mole) of aluminum chloride in 400 ml. of dry benzene. After the addition was complete the mixture was refluxed one hour and then poured onto cracked ice. The organic layer was separated and the aqueous layer was extracted with benzene. The combined extracts were dried over magnesium sulfate and the solvent was evaporated at reduced pressure. The residual oil which did not crystallize on cooling was distilled at reduced pressure and the fraction boiling at 160°–170° C./0.05 mm. collected. The crude product weighed 50 g. A mixture of 50 g. of the crude 1-acetyl-3-benzoylpyrrolidine and 200 ml. of 6 N hydrochloric acid was refluxed 12 hours, cooled and extracted with benzene. The combined extracts were washed with water, dried over magnesium sulfate and the solvent evaporated at reduced pressure. The residual oil weighed 15.1 g. (16% yield). A portion (2.5 g.) of the free base was dissolved in 50 ml. of isopropanol and treated with ethereal hydrogen chloride. The white crystalline salt which formed weighed 2.4 g. and melted at 193°–195° C.

ii. Employing the appropriate N-acetylamino acid in place of N-acetylnipecotic acid and benzene or the appropriately substituted benzene in each case, the following compounds are obtained by the above procedure. When R⁸ is OH the starting material is the corresponding acetate and the final product is obtained after hydrolysis, if desired.

$$\begin{array}{c} \text{HN} \overset{(CH_2)_a}{\underset{(CH_2)_n}{\diagup\hspace{-0.3em}\diagdown}} \underset{O}{\overset{\phantom{|}}{\text{CHCC}_6\text{H}_4\text{R}^8}} \end{array}$$

| a | n | R⁸ | a | n | R⁸ |
|---|---|-----|---|---|-----|
| 1 | 2 | H | 2 | 2 | 4-CF₃ |
| 1 | 2 | 4-Br | 2 | 2 | 2-CH₃O |
| 1 | 2 | 4-OH | 2 | 3 | 4-F |
| 1 | 3 | H | 2 | 3 | 3-CH₃SO₂ |
| 1 | 3 | 2-Cl | 3 | 3 | 4-OH |
| 1 | 3 | 4-Cl | 3 | 3 | 4-F |

PREPARATION M

N-(1,4-Benzodioxan-2-carbonyl)piperazine 1,4-Benzodioxan-2-carboxylic acid, prepared by oxidation of 2-hydroxymethyl-1,4-benzodioxan with potassium permanganate in aqueous potassium hydroxide at 5°–15° C., was converted to the acid chloride by reaction with thionyl chloride in the standard manner.

A suspension of piperazine (11.88 g.) and sodium acetate (20.30 g.) in a mixture of water (70 ml.) and acetone (95 ml.) was stirred at 10°–15° C., then concentrated hydrochloric acid was added (about 35 ml.) until the pH of the solution reached 1.5. 1,4-Benzodioxan-2-carbonyl chloride (31.0 g.) and sodium hydroxide (5 N, about 45 ml.) were then added portionwise while maintaining the temperature at 10°–15° C., the sodium hydroxide maintaining the pH at 1.7–2.2. After the addition was complete, the pH was adjusted to 2.0 by the addition of sodium hydroxide, the suspension was stirred for a further 30 minutes. Water was then added until a homogeneous solution resulted, the acetone removed in vacuo, and the aqueous phase was basified to pH 8–9 with sodium hydroxide (5 N), re-extracted with chloroform (3×200 ml.) and the extracts washed with water, dried (MgSO₄) and evaporated in vacuo. The oily residue was dissolved in ethyl acetate, treated with ethereal hydrogen chloride, evaporated in vacuo and the solid residue triturated with ether, followed by recrystallization from methanol to give N-(1,4-benzodioxan-2-carbonyl)piperazine hydrochloride (4.85 g.), M.P. 265°–267° C.

PREPARATION N

N-Acetyl-4-allyloxypiperidine

A solution of N-acetyl-4-hydroxypiperidine (100 g.) in dimethylformamide (250 ml.) was added dropwise to sodium hydride (38 g., 50% mineral oil dispersion) under an atmosphere of nitrogen. The mixture was stirred for 2 hours then allyl bromide (93 g.) was added slowly whilst maintaining the reaction temperature at 25° C. by external cooling. The mixture was then stirred at room temperature overnight, diluted with isopropanol (20 ml.) and ether (500 ml.), filtered, and evaporated in vacuo. Distillation of the residue gave N-acetyl-4-allyloxypiperidine (108.8 g.), B.P. 128° C./2 mm., identified spectroscopically.

PREPARATION O 4-(2-Methoxy-n-propoxy)piperidine

A solution of N-acetyl-4-allyloxypiperidine (6.4 g.) in dry methanol (10 ml.) is added dropwise to a stirred suspension of mercuric acetate (11.5 g.) in methanol (50 ml.) at room temperature. After 20 minutes the mercuric acetate is dissolved and the mixture is stirred for a further 40 minutes, cooled in ice-water, and sodium hydroxide (20 ml., 5 N) is then added. A yellow precipitate formed during the addition. A solution of sodium borohydride (1.3 g.) in sodium hydroxide (20 ml., 5 N) is then added, the mixture stirred for 10 minutes, and acetic acid added to bring the pH to 6. The mixture is filtered from precipitated mercury, the ethanol evaporated in vacuo, and the resulting aqueous phase extracted with chloroform.

The organic extracts are dried ($Na_2SO_4$), evaporated in vacuo, and the resulting crude residue taken up in methanol (50 ml.) and heated under reflux overnight with sodium hydroxide (20 ml., 5 N) and water (20 ml.). Most of the alcohol is then removed in vacuo, the aqueous layer extracted with ether, the extracts dried ($Na_2SO_4$) and evaporated to leave a residue. The residue is treated with hydrochloric acid (20 ml., 2 N) and heated on a steam bath for 10 hours. The mixture is then washed with ether, the aqueous phase basified ($Na_2CO_3$), extracted with ether and the organic extract dried ($Na_2SO_4$) and evaporated to leave a resiude. Distillation of the residue at reduced pressure affords the title compound.

PREPARATION P

4-(2-Hydroxy-n-propoxy)piperidine

N-Acetyl-4-allyloxypiperidine (18 g.) in tetrahydrofuran (30 ml.) was added dropwise to a stirred yellow suspension of mercuric acetate (34 g.) in a mixture of water (120 ml.) and tetrahydrofuran (120 ml.). The suspension dissolved during the addition and the resulting clear solution was stirred at room temperature for 20 minutes, then sodium hydroxide (70 ml., 5 N) was added, accompanied by ice/water cooling. The intermediate thus obtained was then reduced by the addition of sodium borohydride (2 g.) in sodium hydroxide (40 ml., 5 N), the excess hydride being destroyed after 10 minutes with glacial acetic acid. The liquid phase was then decanted off, saturated with sodium chloride, the organic phase separated, and the remaining aqueous layer extracted four times with chloroform. The combined organic phases were dried ($Na_2SO_4$), and evaporated in vacuo to leave a colorless oil (23 g.).

This oil was stirred with 5 N sodium hydroxide at room temperature for 16 hours, then at 100° C. for 2 hours. The solution was then extracted with chloroform (four times), the combined extracts dried ($Na_2SO_4$), and evaporated in vacuo to leave a crude crystalline product (16.1 g.). This was taken up in methylene chloride, filtered, evaporated, and the residue triturated with petroleum ether (B.P. 40°/60° C.) to yield 4-(2-hydroxy-n-propoxy)piperidine (11.0 g.), M.P. 55°–57° C. The oxalate salt thereof was prepared by combining ethereal solutions of the two reactants and recrystallized from isopropanol, M.P. 104°–105° C.

PREPARATION Q

4-(3-Methoxypropoxy)piperidine

A solution of N-acetyl-4-hydroxypiperidine (30.5 g.) in dimethylformamide (200 ml.) is added dropwise to a stirred suspension of sodium hydride (11.26 g., 50% dispersion in mineral oil) in dimethylformamide (300 ml.) under an atmosphere of nitrogen. The reaction temperature is kept below 30° C. by external cooling and, after the addition is complete, stirring is continued for a further 1¼ hours. A solution of 1-bromo-3-methoxypropane (35.2 g.) in dimethylformamide (100 ml.) is then added dropwise with external cooling, and the resulting clear solution is stirred at room temperature overnight. The reaction mixture is then evaporated in vacuo, the residue partitioned between water and chloroform, the organic extracts dried ($Na_2SO_4$) and evaporated to leave a crude residue. The above aqueous phase is saturated with sodium chloride, further extracted with chloroform, and the organic phase is dried ($Na_2SO_4$), and evaporated to leave a further residue. This residue is combined with the original residue and heated on a steam bath overnight with hydrochloric acid (243 ml., 2 N). The reaction mixture is extracted with chloroform to remove the residual mineral oil, the aqueous phase concentrated, basified with sodium hydroxide (pH 12), then reextracted with chloroform. The organic extracts are washed with brine, dried ($Na_2SO_4$) and evaporated to afford the desired product.

We claim:

1. A compound of the formula

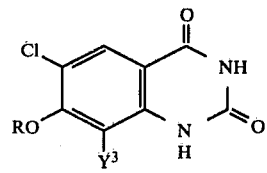

wherein $Y^3$ is hydrogen or OR and R is alkyl having from 1 to 3 carbon atoms.

2. The compound of claim 1 wherein $Y^3$ is methoxy and R is methyl.

3. The compound of claim 1 wherein $Y^3$ is hydrogen and R is methyl.

* * * * *